(12) United States Patent
Hunsley et al.

(10) Patent No.: US 12,429,478 B2
(45) Date of Patent: *Sep. 30, 2025

(54) SUSPENSION COMPOSITION FOR HEMATOLOGY ANALYSIS CONTROL

(71) Applicant: STRECK LLC, La Vista, NE (US)

(72) Inventors: Brad Hunsley, Papillion, NE (US); John W. Scholl, Omaha, NE (US)

(73) Assignee: STRECK LLC, La Vista, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/973,220

(22) Filed: Oct. 25, 2022

(65) Prior Publication Data
US 2023/0228742 A1 Jul. 20, 2023

Related U.S. Application Data

(63) Continuation of application No. 16/321,747, filed as application No. PCT/US2017/044368 on Jul. 28, 2017, now Pat. No. 11,506,655.

(60) Provisional application No. 62/454,224, filed on Feb. 3, 2017, provisional application No. 62/368,676, filed on Jul. 29, 2016.

(51) Int. Cl.
G01N 33/50 (2006.01)
C12N 5/078 (2010.01)

(52) U.S. Cl.
CPC ....... *G01N 33/5094* (2013.01); *C12N 5/0634* (2013.01); *C12N 2501/90* (2013.01); *C12N 2501/999* (2013.01)

(58) Field of Classification Search
None
See application file for complete search history.

(56) References Cited

U.S. PATENT DOCUMENTS

| | | |
|---|---|---|
| 1,432,249 A | 10/1922 | Hoyme |
| 1,922,799 A | 8/1933 | Gaus |
| 2,250,666 A | 7/1941 | Godefroy |
| 2,690,624 A | 10/1954 | Phillips |
| 2,930,570 A | 3/1960 | Leedy |
| 3,781,120 A | 12/1973 | Engelhardt |
| 3,867,521 A | 2/1975 | Miskel et al. |
| 3,872,730 A | 3/1975 | Ringrose et al. |
| 3,874,384 A | 4/1975 | Deindoerfer et al. |
| 3,879,295 A | 4/1975 | Glover et al. |
| 3,973,913 A | 8/1976 | Louderback |
| 3,982,007 A | 9/1976 | Laber et al. |
| 3,994,085 A | 11/1976 | Groselak et al. |
| 4,043,453 A | 8/1977 | Greenlee |
| 4,160,644 A | 7/1979 | Ryan |
| 4,318,090 A | 3/1982 | Narlow et al. |
| 4,436,821 A | 3/1984 | Ryan |
| 4,513,522 A | 4/1985 | Selenke |
| 4,515,890 A | 5/1985 | Manderino et al. |
| 4,579,759 A | 4/1986 | Breuers |
| 4,584,219 A | 4/1986 | Baartmans |
| 4,675,159 A | 6/1987 | Al-Sioufi |
| 4,704,364 A | 11/1987 | Carver et al. |
| 4,818,700 A | 4/1989 | Cregg et al. |
| 4,884,827 A | 12/1989 | Kelley |
| 4,921,277 A | 5/1990 | Mcdonough |
| 5,000,484 A | 3/1991 | Phelan et al. |
| 5,060,672 A | 10/1991 | Irimi et al. |
| 5,110,908 A | 5/1992 | Deich et al. |
| 5,135,125 A | 8/1992 | Andel et al. |
| 5,196,182 A | 3/1993 | Ryan |
| 5,213,765 A | 5/1993 | Kasai et al. |
| 5,250,438 A | 10/1993 | Ryan |
| 5,257,633 A | 11/1993 | Vogler et al. |
| 5,260,048 A | 11/1993 | Ryan |
| 5,262,327 A | 11/1993 | Ryan |
| 5,270,208 A | 12/1993 | Ryan |
| 5,343,647 A | 9/1994 | Bulka |
| 5,366,249 A | 11/1994 | Diemert |
| 5,432,089 A | 7/1995 | Ryan et al. |
| 5,447,842 A | 9/1995 | Simons |
| 5,457,024 A | 10/1995 | Goldbard |
| 5,459,073 A | 10/1995 | Ryan |
| 5,459,253 A | 10/1995 | Wolin et al. |
| 5,460,797 A | 10/1995 | Ryan |
| 5,468,022 A | 11/1995 | Linder et al. |
| 5,490,658 A | 2/1996 | Coward et al. |
| 5,501,954 A | 3/1996 | Mahr et al. |
| 5,512,343 A | 4/1996 | Shaw |

(Continued)

FOREIGN PATENT DOCUMENTS

| | | |
|---|---|---|
| CA | 2406463 A1 | 11/2001 |
| CN | 104634628 A | 5/2015 |

(Continued)

OTHER PUBLICATIONS

Okamoto et al. Carbohydrate Polym, Applied Science vol. 53 (3) pp. 337-342 (Year: 2003).*
Diamond et al., Diverse and Targetable Kinase Alterations Drive Histiocytic Neoplasms, Cancer discovery, 6(2):154-65 (2016).
Ding, et al., MS Analysis of Single-Nucleotide, Differences in Circulating Nucleic Acids: Application to Noninvasive Prenatal Diagnosis, Proc. Natl. Acad. Sci. USA, 101:10762-10767 (2004).
Dumaswala et al., Improved red blood cell preservation correlates with decreased loss of bands 3, 4.1, acetylcholinestrase, and lipids in microvesicles, Blood, 87(4):1612-6 (1996).

(Continued)

*Primary Examiner* — Blaine Lankford
(74) *Attorney, Agent, or Firm* — MARSHALL, GERSTEIN & BORUN LLP

(57) ABSTRACT

A suspension composition for a hematology analysis control particularly useful for preserving relevant detectable characteristics of blood cells for a prolong stability period. The suspension may include at least one polysaccharide, which may include or derive from chitosan and/or chitin, as a stabilizing agent.

21 Claims, 4 Drawing Sheets

(56) References Cited

U.S. PATENT DOCUMENTS

| | | |
|---|---|---|
| 5,512,485 A | 4/1996 | Young et al. |
| 5,538,871 A | 7/1996 | Nuovo et al. |
| 5,540,358 A | 7/1996 | Wiles et al. |
| 5,560,657 A | 10/1996 | Morgan |
| 5,614,391 A | 3/1997 | Franciskovich et al. |
| 5,618,664 A | 4/1997 | Kiessling |
| 5,629,147 A | 5/1997 | Asgari et al. |
| D382,343 S | 8/1997 | Wandell et al. |
| 5,654,054 A | 8/1997 | Tropsha et al. |
| 5,688,516 A | 11/1997 | Raad et al. |
| 5,731,156 A | 3/1998 | Golbus |
| 5,741,638 A | 4/1998 | Yamane |
| 5,783,093 A | 7/1998 | Holme |
| 5,811,099 A | 9/1998 | Ryan |
| 5,817,519 A | 10/1998 | Zelmanovic et al. |
| 5,849,517 A | 12/1998 | Ryan |
| 5,858,699 A | 1/1999 | Granger et al. |
| 5,858,790 A | 1/1999 | Kim et al. |
| 5,861,253 A | 1/1999 | Asgari et al. |
| 5,888,822 A | 3/1999 | Hengstenberg |
| 5,906,744 A | 5/1999 | Carroll et al. |
| 5,962,234 A | 10/1999 | Golbus |
| 5,976,014 A | 11/1999 | Petrick et al. |
| 5,977,153 A | 11/1999 | Camiener |
| 5,985,572 A | 11/1999 | Macfarlane |
| 6,013,240 A | 1/2000 | Behr et al. |
| 6,030,767 A | 2/2000 | Wagner et al. |
| 6,043,032 A | 3/2000 | Yamagishi |
| 6,072,086 A | 6/2000 | James et al. |
| 6,074,827 A | 6/2000 | Nelson et al. |
| 6,077,235 A | 6/2000 | Serpentino et al. |
| 6,125,563 A | 10/2000 | Girerd |
| 6,128,840 A | 10/2000 | Boisvert |
| 6,168,922 B1 | 1/2001 | Harvey et al. |
| 6,177,163 B1 | 1/2001 | Blok et al. |
| 6,187,590 B1 * | 2/2001 | Kim ................ G01N 33/5002 436/166 |
| 6,190,609 B1 | 2/2001 | Chapman et al. |
| 6,197,539 B1 | 3/2001 | Granger et al. |
| 6,197,540 B1 | 3/2001 | Granger et al. |
| 6,200,500 B1 | 3/2001 | Ryan |
| 6,210,889 B1 | 4/2001 | Drouin et al. |
| 6,218,531 B1 | 4/2001 | Ekenberg |
| 6,221,668 B1 | 4/2001 | Ryan et al. |
| 6,251,638 B1 | 6/2001 | Umansky et al. |
| 6,258,540 B1 | 7/2001 | Lo et al. |
| 6,287,820 B1 | 9/2001 | Umansky et al. |
| 6,337,189 B1 | 1/2002 | Ryan |
| 6,365,362 B1 | 4/2002 | Terstappen et al. |
| 6,399,388 B1 | 6/2002 | Ryan et al. |
| 6,403,377 B1 | 6/2002 | Ryan et al. |
| 6,406,915 B2 | 6/2002 | Ryan et al. |
| 6,514,763 B2 | 2/2003 | Carver et al. |
| 6,527,242 B1 | 3/2003 | Kennedy |
| 6,527,957 B1 | 3/2003 | Deniega et al. |
| 6,551,267 B1 | 4/2003 | Cohen et al. |
| 6,560,847 B2 | 5/2003 | Ohlsson |
| 6,579,672 B1 | 6/2003 | Granger et al. |
| 6,581,973 B2 | 6/2003 | Levine et al. |
| 6,602,718 B1 | 8/2003 | Augello et al. |
| 6,617,170 B2 | 9/2003 | Augello et al. |
| 6,617,180 B1 | 9/2003 | Wang |
| 6,623,983 B1 | 9/2003 | Terstappen et al. |
| 6,630,301 B1 | 10/2003 | Gocke et al. |
| 6,645,731 B2 | 11/2003 | Terstappen et al. |
| 6,653,063 B2 | 11/2003 | Carver et al. |
| 6,664,056 B2 | 12/2003 | Lo et al. |
| 6,723,563 B2 | 4/2004 | Ryan |
| 6,759,217 B2 | 7/2004 | Kopreski |
| 6,821,789 B2 | 11/2004 | Augello et al. |
| 6,860,513 B2 | 3/2005 | Kaufman |
| 6,884,573 B2 | 4/2005 | Fischer et al. |
| 6,913,932 B2 | 7/2005 | Maples et al. |
| 6,916,634 B2 | 7/2005 | Kopreski |
| 6,939,671 B2 | 9/2005 | Kopreski |
| 6,994,790 B2 | 2/2006 | Corbin et al. |
| 7,022,478 B2 | 4/2006 | Rainer et al. |
| 7,044,941 B2 | 5/2006 | Mathias et al. |
| 7,208,275 B2 | 4/2007 | Gocke et al. |
| 7,267,980 B1 | 9/2007 | Mortari et al. |
| 7,282,371 B2 | 10/2007 | Helftenbein |
| 7,288,380 B1 | 10/2007 | Gocke et al. |
| 7,318,293 B2 | 1/2008 | Ardern, II |
| 7,332,277 B2 | 2/2008 | Dhallan |
| 7,332,288 B2 | 2/2008 | Terstappen et al. |
| 7,358,039 B2 | 4/2008 | Fischer et al. |
| 7,390,663 B2 | 6/2008 | Ryan et al. |
| 7,398,999 B2 | 7/2008 | Kaufman |
| 7,419,832 B2 | 9/2008 | Hunsley et al. |
| 7,442,506 B2 | 10/2008 | Dhallan |
| 7,445,901 B2 | 11/2008 | Kudlicki et al. |
| 7,478,513 B2 | 1/2009 | Baldwin |
| 7,569,350 B2 | 8/2009 | Gocke et al. |
| 7,651,838 B2 | 1/2010 | Paterlini-Brechot |
| 7,727,720 B2 | 6/2010 | Dhallan |
| 7,767,460 B2 | 8/2010 | Hunsley et al. |
| 8,304,187 B2 | 11/2012 | Fernando |
| 8,546,144 B2 | 10/2013 | Das et al. |
| 8,551,784 B2 | 10/2013 | Das et al. |
| 8,586,306 B2 | 11/2013 | Fernando |
| 8,841,077 B2 | 9/2014 | Paige et al. |
| 9,034,635 B2 | 5/2015 | Termaat et al. |
| 9,040,255 B2 | 5/2015 | Tsinberg et al. |
| 9,120,849 B2 | 9/2015 | Chiklis et al. |
| 9,127,048 B2 | 9/2015 | Chiklis et al. |
| 9,657,227 B2 | 5/2017 | Fernando |
| 9,926,590 B2 | 3/2018 | Fernando |
| 9,926,950 B2 | 3/2018 | Ooki et al. |
| 9,956,281 B2 | 5/2018 | Ryan et al. |
| 10,006,861 B2 | 6/2018 | Kreifels et al. |
| 10,091,984 B2 | 10/2018 | Fernando et al. |
| 10,144,955 B2 | 12/2018 | Fernando |
| 10,294,513 B2 | 5/2019 | Fernando |
| 11,506,655 B2 * | 11/2022 | Hunsley ............ G01N 33/5094 |
| 2001/0018192 A1 | 8/2001 | Terstappen et al. |
| 2001/0049895 A1 | 12/2001 | Burke |
| 2001/0051341 A1 | 12/2001 | Lo et al. |
| 2002/0045196 A1 | 4/2002 | Mahoney et al. |
| 2002/0066216 A1 | 6/2002 | Delacruz |
| 2002/0086346 A1 | 7/2002 | Ryan |
| 2002/0119503 A1 | 8/2002 | Ryan et al. |
| 2003/0104631 A1 | 6/2003 | Carver et al. |
| 2003/0232377 A1 | 12/2003 | Thomas |
| 2004/0014107 A1 | 1/2004 | Garcia-Blanco et al. |
| 2004/0038424 A1 | 2/2004 | Maples |
| 2004/0137417 A1 | 7/2004 | Ryan |
| 2005/0029559 A9 | 2/2005 | Ahn et al. |
| 2005/0049793 A1 | 3/2005 | Paterlini-Brechot |
| 2005/0107316 A1 | 5/2005 | Strebhardt et al. |
| 2005/0164241 A1 | 7/2005 | Hahn et al. |
| 2005/0181353 A1 | 8/2005 | Rao et al. |
| 2005/0181463 A1 | 8/2005 | Rao et al. |
| 2005/0232377 A1 | 10/2005 | Kutz et al. |
| 2005/0277204 A1 | 12/2005 | Hollis et al. |
| 2006/0008807 A1 | 1/2006 | O'Hara et al. |
| 2006/0105372 A1 | 5/2006 | Bair et al. |
| 2006/0194192 A1 | 8/2006 | Rao et al. |
| 2006/0210429 A1 | 9/2006 | Hunsley et al. |
| 2007/0111233 A1 | 5/2007 | Bianchi et al. |
| 2007/0134658 A1 | 6/2007 | Bohmer |
| 2007/0178478 A1 | 8/2007 | Dhallan et al. |
| 2007/0202525 A1 | 8/2007 | Quake et al. |
| 2007/0243548 A1 | 10/2007 | Georges et al. |
| 2007/0243549 A1 | 10/2007 | Bischoff |
| 2007/0251337 A1 | 11/2007 | Reed et al. |
| 2007/0298406 A1 | 12/2007 | Martorell et al. |
| 2008/0020390 A1 | 1/2008 | Mitchell et al. |
| 2008/0057502 A1 | 3/2008 | Kopreski |
| 2008/0081689 A1 | 4/2008 | Seelig et al. |
| 2008/0096217 A1 | 4/2008 | Kopreski |
| 2008/0102470 A1 | 5/2008 | Dawson et al. |
| 2008/0108071 A1 | 5/2008 | Thompson |
| 2008/0119645 A1 | 5/2008 | Griffey et al. |
| 2008/0206866 A1 | 8/2008 | Zieglschmid et al. |

(56) References Cited

U.S. PATENT DOCUMENTS

| | | |
|---|---|---|
| 2008/0261292 A1 | 10/2008 | Kopreski |
| 2008/0318801 A1 | 12/2008 | Leung |
| 2009/0034446 A1 | 2/2009 | Adams et al. |
| 2009/0081678 A1 | 3/2009 | Ryan et al. |
| 2009/0215036 A1 | 8/2009 | Stropp et al. |
| 2009/0269799 A1 | 10/2009 | Winkelman et al. |
| 2009/0308303 A1 | 12/2009 | Burlando |
| 2010/0167271 A1 | 7/2010 | Ryan |
| 2010/0184069 A1 | 7/2010 | Fernando et al. |
| 2010/0190796 A1 | 7/2010 | Verkman et al. |
| 2010/0209930 A1 | 8/2010 | Fernando |
| 2010/0216153 A1 | 8/2010 | Lapidus et al. |
| 2010/0317107 A1 | 12/2010 | Ryan |
| 2011/0014645 A1 | 1/2011 | Winkelman et al. |
| 2011/0027771 A1 | 2/2011 | Deng |
| 2011/0053208 A1 | 3/2011 | Reiss et al. |
| 2011/0110975 A1 | 5/2011 | Grunkemeyer et al. |
| 2011/0111410 A1 | 5/2011 | Ryan et al. |
| 2012/0164676 A1 | 6/2012 | Tsinberg et al. |
| 2012/0308985 A1* | 12/2012 | Ryan .............. G01N 33/96 |
| | | 435/372 |
| 2012/0308990 A1 | 12/2012 | Termaat et al. |
| 2013/0034860 A1 | 2/2013 | Fernando |
| 2013/0070077 A1 | 3/2013 | Winkelman et al. |
| 2013/0077085 A1 | 3/2013 | Zahniser et al. |
| 2013/0209985 A1 | 8/2013 | Hoke et al. |
| 2014/0054508 A1 | 2/2014 | Fernando |
| 2014/0080112 A1 | 3/2014 | Ryan et al. |
| 2014/0199681 A1 | 7/2014 | Ryan et al. |
| 2015/0030578 A1 | 1/2015 | Releford et al. |
| 2015/0301037 A1 | 10/2015 | Tsinberg et al. |
| 2016/0143268 A1 | 5/2016 | Ryan |
| 2016/0174544 A1 | 6/2016 | Fernando et al. |
| 2017/0052173 A1 | 2/2017 | Hunsley et al. |
| 2017/0097361 A1 | 4/2017 | Alt et al. |
| 2017/0145475 A1 | 5/2017 | Hunsley et al. |
| 2018/0243406 A1 | 8/2018 | Ryan et al. |
| 2019/0127780 A1 | 5/2019 | Hunsley et al. |
| 2019/0177774 A1 | 6/2019 | Connelly et al. |

FOREIGN PATENT DOCUMENTS

| | | |
|---|---|---|
| CN | 107525818 A | 12/2017 |
| DE | 19928820 A1 | 12/2000 |
| EP | 1031626 A1 | 8/2000 |
| EP | 1207208 A2 | 5/2002 |
| EP | 1212613 A1 | 6/2002 |
| EP | 1217372 A1 | 6/2002 |
| EP | 1425294 A2 | 6/2004 |
| EP | 1816461 A1 | 8/2007 |
| EP | 1889921 A2 | 2/2008 |
| EP | 2216416 A1 | 8/2010 |
| EP | 2228453 A1 | 9/2010 |
| EP | 2411808 A2 | 2/2012 |
| EP | 2674502 A1 | 12/2013 |
| EP | 2704740 A2 | 3/2014 |
| EP | 2814981 A2 | 12/2014 |
| EP | 3118623 A1 | 1/2017 |
| EP | 3225699 A1 | 10/2017 |
| EP | 3572531 A1 | 11/2019 |
| JP | 4453999 B2 | 4/2010 |
| WO | 90/10715 A1 | 9/1990 |
| WO | 93/05650 A1 | 4/1993 |
| WO | 94/02646 A1 | 2/1994 |
| WO | 95/26417 A1 | 10/1995 |
| WO | 98/02528 A1 | 1/1998 |
| WO | 98/02740 A1 | 1/1998 |
| WO | 98/59042 A1 | 12/1998 |
| WO | 00/00813 A1 | 1/2000 |
| WO | 00/06780 A1 | 2/2000 |
| WO | 00/75647 A1 | 12/2000 |
| WO | 00/77235 A1 | 12/2000 |
| WO | 01/14872 A1 | 3/2001 |
| WO | 01/79851 A1 | 10/2001 |
| WO | 01/98542 A2 | 12/2001 |
| WO | 02/55985 A2 | 7/2002 |
| WO | 02/56030 A2 | 7/2002 |
| WO | 03/18757 A2 | 3/2003 |
| WO | 03/19141 A2 | 3/2003 |
| WO | 03/69344 A1 | 8/2003 |
| WO | 2003/074723 A2 | 9/2003 |
| WO | 03/95974 A2 | 11/2003 |
| WO | 2006/100063 A2 | 9/2006 |
| WO | 2007/022483 A2 | 2/2007 |
| WO | 2008/107724 A2 | 9/2008 |
| WO | 2008/111981 A1 | 9/2008 |
| WO | 2009/105499 A1 | 8/2009 |
| WO | 2010/078194 A1 | 7/2010 |
| WO | 2010/096323 A1 | 8/2010 |
| WO | 2010/111388 A2 | 9/2010 |
| WO | 2010/123908 A1 | 10/2010 |
| WO | 2010/132756 A2 | 11/2010 |
| WO | 2011/014741 A1 | 2/2011 |
| WO | 2011/057184 A1 | 5/2011 |
| WO | 2011/082415 A2 | 7/2011 |
| WO | 2012/145662 A1 | 10/2012 |
| WO | 2012/151391 A2 | 11/2012 |
| WO | 2012/166913 A1 | 12/2012 |
| WO | 2013/016038 A1 | 1/2013 |
| WO | 2013/019290 A2 | 2/2013 |
| WO | 2013/086428 A1 | 6/2013 |
| WO | 2013/123030 A2 | 8/2013 |
| WO | 2014/029791 A1 | 2/2014 |
| WO | 2015/134053 A1 | 9/2015 |
| WO | 2017/031354 A2 | 2/2017 |
| WO | 2017/201612 A1 | 11/2017 |
| WO | 2017/218789 A1 | 12/2017 |
| WO | 2018/022991 A1 | 2/2018 |
| WO | 2018/031903 A1 | 2/2018 |
| WO | 2018/035340 A1 | 2/2018 |
| WO | 2019/079743 A1 | 4/2019 |
| WO | 2019/090126 A1 | 5/2019 |
| WO | 2020/140035 A1 | 7/2020 |

OTHER PUBLICATIONS

EP Application No. 10000518.0 (Patent No. EP2228453), Brief communication regarding Letter from the opponent 02 (Cenata) of Jun. 6, 2018 including exhibits, dated Jun. 14, 2018.
EP Application No. 10000518.0 (Patent No. EP2228453), Brief communication to Opponent 1 and Opponent 2 dated May 29, 2018 and Reply including exhibits of patent proprietor to notice(s) of opposition dated Apr. 26, 2018.
European application No. 03 256 535.0-2113, Decision to refuse a European Patent application, Mailed May 30, 2007.
European Application No. 10000518.0, Communication of a notice of intervention including exhibits by Cenata GmbH, mailed Apr. 13, 2018.
European Application No. 10000518.0, Communication of a notice of opposition including exhibits, mailed Sep. 12, 2017.
European Application No. 10704474.5, European Patent Office Summons to Attend, mailed Jan. 27, 2016.
European Application No. 10704474.5, European Third Party Observations, mailed Aug. 30, 2016.
European Application No. 13706856.5, European Communication of a notice of opposition including exhibits, mailed Mar. 28, 2018.
European Application No. 13706856.5, European Third Party Observations, mailed May 25, 2016.
European Application No. EP 17 84 2131, Supplementary partial search report, mailed Mar. 16, 2020.
Fairbrother et al., Clinical experience of noninvasive prenatal testing with cell-free DNA for fetal trisomies 21, 18, and 13, in a general screening population, Prenatal Diagnosis, 33(6):580-3 (2013).
Fernando et al., A new methodology to preserve the original proportion and integrity of cell-free fetal DNA in maternal plasma during sample processing and storage, 30(5):418-424 (2010).
Fernando et al., Stabilization of cell-free RNA in blood samples using a new collection device, Clinical Biochemistry, 45(16-17):1497-1502 (2012).

(56) References Cited

OTHER PUBLICATIONS

Fernando et al., Stabilization of cell-free RNA in plasma for noninvasive diagnosis and prognosis, retrieved from the internet: URL: http://www.streck.com/resources/cell_stabilization/cell-free_RNA_BCT_Stabilization_of_Cell-Free_RNA_in_Plasma.pdf (2010).
Funasaki et al., Mechanisms and surface chemical prediction of imipramine-induced hemolysis suppressed by modified cyclodextrins, J. Pharm. Sci., 90(8):1056-65 (2001).
Futch et al., Initial clinical laboratory experience in noninvasive prenatal testing for fetal aneuploidy from maternal plasma DNA samples, Prenatal Diagnosis, 33(6):569-74 (2013).
Gheinani et al., Improved isolation strategies to increase the yield and purity of human urinary exosomes for biomarker discovery, Scientific Reports, 8:3945 (2018).
Gielis et al., Cell-Free DNA: An Upcoming Biomarker in Transplantation, Am. J. Transplant., 15(10):2541-51 (2015).
Gil et al., Cell-free DNA analysis for trisomy risk assessment in first-trimester twin pregnancies, Fetal Diagnosis and Therapy, 35(3):204-11 (2013).
Gil et al., Implementation of maternal blood cell-free DNA testing in early screening for aneuploidies, Ultrasound in Obstetrics & Gynecology, 42(1):34-40 (2013).
Gil et al., UK NHS pilot study on cell-free DNA testing in screening for fetal trisomies: factors affecting uptake, Ultrasound in Obstetrics & Gynecology, 45(1):67-73 (2015).
Gonzales et al., Application of Fetal. DNA Detection in Maternal Plasma: A Prenatal Diagnosis Unit Experience, Journal of Histochemistry & Cytochemistry, 53(3):307-314 (2005).
Greenwalt et al., Erythrocyte membrane vesiculation and changes in membrane composition during storage in citrate-phosphate-dextrose-adenine-1, Vox Sang., 47(4):261-70 (1984).
Grolz et al., Liquid biopsy preservation solutions for standardized pre-analytical workflows-venous whole blood and plasma, Curr. Pathobiol. Rep., 6(4):275-286 (2018).
Gromminger et al., Fetal aneuploidy detection by cell-free DNA sequencing for multiple pregnancies and quality issues with vanishing twins, Journal of Clinical Medicine, 3(3):679-92 (2014).
Gross et al., Rapid changes in circulating tumor cells following anti-angiogenic therapy, Convergent Science Physical Oncology, 1(1):015002 (2015).
Gyorgy et al., Improved circulating microparticle analysis in acid-citrate dextrose (ACD) anticoagulant tube, Thromb Res., 133(2):285-92 (2014).
Haaland, Molecules and models: the molecular structures of main group element compounds Oxford University Press, (abstract available at http://www.oxfordscholarship.com/view/10.1093/acprof:oso/9780199235353.001.0001/acprof-9780199235353-chapter-12) (2018).
Hallick et al., Use of Aurintricarboxylic Acid as in Inhibitor of Nucleases During Nucleic Acid Isolation, Nucleic Acid Research, 4:3055-3064 (1977).
Hanessian et al., The Synthesis of functionalized cyclodextrins as scaffolds and templates for molecular diversity, Catalysis, and Inclusion Phenomena, J. Org. Chem., 60(15): 4786^t797 (1995).
Hidestrand et al., Influence of temperature during transportation on cell-free DNA analysis, Fetal diagnosis and Therapy, 31(2):122-8 (2012).
Hindson et al., High-throughput droplet digital PCR system for absolute quantitation of DNA copy number, Analytica Chemistry, 83(22):8604-10 (2011).
Holford et al., Stability of beta-actin mRNA in plasma, Annals of the New York Academy of Science, 1137:108-111 (2008).
Holmberg et al., Akonni TruTip((Registered)) and Qiagen((Registered)) methods for extraction of fetal circulating DNA—evaluation by real-time and digital PCR, PloS One, 8(8):e73068 (2013).
Hooks et al., Non-invasive risk assessment of fetal sex chromosome aneuploidy through directed analysis and incorporation of fetal fraction, Prenatal Diagnosis, 34(5):496-9 (2014).
Hynek et al., MoM-based Approach to Noninvasive Prenatal Testing Using Exponentially Weighted. Moving Average Chart and Chromosomal Fingerprint, International Journal of Biomedicine and Healthcare, 3(2):12-15 (2015).
Ignatiadis et al., Circulating Tumor Cells and Circulating Tumor DNA: Challenges and Opportunities on the Path to Clinical Utility, Clinical. Cancer Research, 21(21):4786-800 (2015).
International Application No. PCT/US17/44368, International Preliminary Report on Patentability, mailed Feb. 7, 2019.
International Application No. PCT/US17/44368, International Search Report and Written Opinion, mailed Oct. 25, 2017.
International Application No. PCT/US2010/023859, International Search Report and Written Opinion, filed Feb. 11, 2010.
International Application No. PCT/US2010/55815, International Search Report and Written Opinion, filed Nov. 8, 2010.
International Application No. PCT/US2013/025912, International Preliminary Report on Patentability, mailed Apr. 25, 2014.
International Application No. PCT/US2013/025912, Written Opinion of the International Preliminary Examining Authority, mailed Jan. 24, 2014.
International Application No. PCT/US2014/047551, International Preliminary Report on Patentability, mailed Dec. 10, 2015.
International Application No. PCT/US2014/047551, International Search Report & Written Opinion, mailed Oct. 23, 2014.
International Application No. PCT/US2018/056747, International Preliminary Report on Patentability, mailed Apr. 30, 2020.
International Application No. PCT/US2018/056747, International Search Report and Written Opinion, mailed Dec. 17, 2018.
Song et al., Non-invasive prenatal testing for fetal aneuploidies in the first trimester of pregnancy, Ultrasound in Obstetrics & Gynecology, 45(1):55-60 (2015).
Sparks et al., Noninvasive prenatal detection and selective analysis of cell-free DNA obtained from maternal blood: evaluation for trisomy 21 and trisomy 18, Americana Journal of Obstetrics and Gynecology, 206(4):319-e1-9 (2012).
Sparks et al., Selective analysis of cell-free DNA in maternal blood for evaluation of fetal trisomy, Prenatal Diagnosis, 32(1):3-9 (2012).
Stokowski et al., Clinical performance of non-invasive prenatal testing (NIPT) using targeted cell-free DNA analysis in maternal plasma with microarrays or next generation sequencing (NGS) is consistent across multiple controlled clinical studies, Prenatal Diagnosis, 35(12):1243-6 (2015).
Streck et al., 1-XP55419765A, Product Summary: Cell-Free DNA(Trademark) BCT, (2009).
Stumm et al., Diagnostic accuracy of random massively parallel sequencing for non-invasive prenatal detection of common autosomal aneuploidies: a collaborative study in Europe, Prenatal Diagnosis, 34(2):185-91 (2014).
Su et al., Detection of a K-ras mutation in urine of patients with colorectal cancer, Cancer Biomarkers, 1(2-3):177-82 (2005).
Swarup et al., Circulating (cell-free) Nucleic Acids—A Promising, Non-invasive Tool for Early Detection of Several Human Diseases, FEBS Letters, 481:795-799 (2007).
Szarvas et al., Determination of Endogenous Formaldehyde Level in Human Blood and Urine by Dimedone-14C Radiometric Method, J. Radioanal. Nucl. Chem., Letters; 106, 357-367 (1986).
Takabayashi et al., Development of Non-invasive Fetal DNA Diagnosis from Maternal Blood, Prenatal Diagnosis, 15:74-77(1995).
Thung et al., Implementation of whole genome massively parallel sequencing for noninvasive prenatal testing in laboratories, Expert Review of Molecular Diagnostics, 15(1 ):111-24 (2015).
Tong et al., Diagnostic developments involving cell-free (circulating) nucleic acids, Clinica. Chimica. Acta., 363(1):187-96 (2006).
Toro et al., Comparison of cell stabilizing blood collection tubes for circulating plasma tumor DNA, Clinical Biochemistry, 48(15):993-8 (2015).
Toro, Detection of PIK3CA Mutations in Plasma Tumor DNA Circulating in Peripheral Blood of Breast Cancer Patients, Thesis submitted for the degree of Master of Science in Molecular and Cellular Biology. Johns Hopkins University, Baltimore, Maryland (2014).
Torrano et al., Vesicle-MaNiA: extracellular vesicles in liquid biopsy and cancer, Curr. Opin. Pharmacol., 29:47-53 (2016).

(56) References Cited

OTHER PUBLICATIONS

Tynan et al., Application of risk score analysis to low-coverage whole genome sequencing data for the noninvasive detection of trisomy 21, trisomy 18, and trisomy 13, Prenatal diagnosis, 36(1):56-62 (2016).
Provisional Application filed on Feb. 3, 2017, by Noble et al., U.S. Appl. No. 62/454,451.
Provisional Application filed on Feb. 3, 2017, by Noble et al., U.S. Appl. No. 62/454,460.
Uekama et al., Protective effects of cyclodextrins on drug-induced hemolysis in vitro, J. Pharmacobiodyn., 4(2):142-4 (1981).
US FDA, Draft Guidance for Industry: Pre-Storage Leukocyte Reduction of Whole Blood and Blood Components Intended for Transfusion, Vaccines, Blood & Biologics, available at: www.fda.gov/biologicsbloodvaccines/guidancecomplianceregulatoryinformation/guidance/blood/ucm076769.htm (2011).
Vandenberghe et al., Non-invasive detection of genomic imbalances in Hodgkin/Reed-Sternberg cells in early and advanced stage Hodgkin's lymphoma by sequencing of circulating cell-free DNA: a technical proof-of-principle study, The Lancet Haematology, 2(2):e55-65 (2015).
Verweij et al., European Non-invasive Trisomy Evaluation (EU-NITE) study: a multicenter prospective cohort study for non-invasive fetal trisomy 21 testing, Prenatal Diagnosis, 33(10):996-1001 (2013).
Vu et al., Genotyping for DQAI and PM loci in urine using PCR-based amplification: Effects of sample volume, storage temperature, preservatives, and aging on DNA extraction and typing, Forensic Science International, 102(1):23-34 (1999).
Wagner, Free DNA—new potential analyte in clinical laboratory diagnostics, Biochem Med (Zagreb), 22(1):24-38 (2012).
Wang et al., Gestational age and maternal weight effects on fetal cell-free DNA in maternal plasma, Prenatal diagnosis, 33(7):662-6 (2013).
Wang et al., Exploring Glycan Markers for Immunotyping and Precision-targeting of Breast Circulating Tumor Cells, Archives of medical research, 46(8):642-50 (2015).
Wang et al., Lipoprotient Lipase: from gene to obesity, Am. J. Physiol. Endocrinol. Met., 297(2):E271-E288 (2009).
Wang et al., Maternal mosaicism is a significant contributor to discordant sex chromosomal aneuploidies associated with noninvasive prenatal testing, Clinical chemistry, 60(1):251-9 (2014).
Wang et al., Real-time PCR evaluation of cell-free DNA subjected to various storage and shipping conditions, Genetics and Molecular Research, 14(4): 12797-804 (2015).
Wang et al., Sensitive detection of mono-and polyclonal ESR1 mutations in primary tumors, metastatic lesions and cell free DNA of breast cancer patients, Clinical Cancer Research, 22(5): 1130-7 (2016).
Weisz et al., Protection of erythrocytes against hemolytic agents by cyclodextrin polysulfate, Biochem Pharmacol., 45 (5):1011-6 (1993).
Werner et al., Analytical Validation and Capabilities of the Epic CTC Platform: Enrichment-Free Circulating Tumour Cell Detection and Characterization, Journal of Circulating Biomarkers, 4:3 (2015).
What are the regulatory Definitions for "Ambient", "Room Temperature" and "Cold Chain" (https://www.gmp-compliance.org/gmp-news/what-are-the-regulatory-definitions-for-ambient-room-temperature-and-cold-chain) (2017).
Wiebe et al., Inhibition of Cell Proliferation by Glycerol, Life Sciences, 48(16):1511-7 (1991).
Wienzek-Lischka et al., Noninvasive fetal genotyping of human platelet antigen-1a using targeted massively parallel sequencing, Transfusion, 55(6 Pt 2):1538-44 (2015).
Willems et al., The first 3,000 non-invasi-s7e prenatal tests (NWT) with the harmony test in Belgium and the Netherlands, Facts, Views & Vision in ObGyn, 6(1):7-12 (2014).
Wolf, The nature and significance of platelet products in human plasma, Br. J. Haematol., 13(3):269-88(1967).

Wong et al., Optimizing blood collection, transport and storage conditions for cell free DNA increases access to prenatal testing, Clin. Biochem., 46(12): 1099-1104 (2013).
Wong et al., The role of physical stabilization in whole blood preservation, Sci. Rep., 6:21023 (2016).
Woolcock et al., Noninvasive prenatal testing, Australian Family Physician, 43(7):432^t (2014).
Yoshida et al., Red blood cell storage lesion: causes and potential clinical consequences, Blood Transfus., 17(1):27-52 (2019).
Zhang et al., Effect of Formaldehyde Treatment on the Recovery of Cell-Free Fetal DNA from Maternal Plasma atCDifferent Processing Times, Clinica Chimica Acta., 397:60-64 (2008).
Zhang, et al., Genotyping of urinary samples stored with EDTA for forensic applications, Genetics and Molecular Research, 11(3):3007-12 (2012).
Zhou et al., Collection, storage, preservation, and normalization of human urinary exosomes for biomarker discovery, Kidney Int., 69(8):1471-1476 (2006).
Zhou et al., Cyclodextrin functionalized polymers as drug delivery, Polymer Chemistry, 1:1552-1559 (2010).
Zill et al., Cell-free DNA next-generation sequencing in pancreatobiliary carcinomas, Cancer discovery, 5(10):1040-8 (2015).
Alvarez et al., Comparison of protein, microRNA, and mRNA yields using different methods of urinary exosome isolation for the discovery of kidney disease biomarkers, Kidney International 82:1024-1032 (2012).
Ames et al., An Appraisal of the "Vacutainer" System for Blood Collection, Ann. Clin. Biochem., 12:151-155 (1975).
Angert et al., Fetal Cell-free Plasma DNA Concentrations in Maternal Blood Are Stable 24 Hours after Collection: Analysis of First- and Third-Trimester Samples, Clinical-Chemistry, 49(1):195-198 (2003).
Arikan, A comparison of the effect of methyl-beta-cyclodextrin on the osmotic fragility of ovine, bovine and human erythrocytes, Turk J. Vet. Anim. Sci., 27:383-387 (2003).
Ashoor et al., Trisomy 13 detection in the first trimester of pregnancy using a chromosome-selective cell-free DNA analysis method, Ultrasound in Obstetrics & Gynecology, 41(1):21-5 (2012).
Barrett et al., Implementing Prenatal Diagnosis Based on Cell-Free Fetal DNA. Accurate Identification of Factors Affecting Fetal DNA Yield, PLoS One, 6(10):e25202 (2011).
Bayindir et al., Noninvasive Prenatal Testing Using a Novel Analysis Pipeline to Screen for All Autosomal Fetal Aneuploidies Improves Pregnancy Management, European Journal of Human Genetics, 23(10):1286-93 (2015).
Beck et al., Digital Droplet PCR for Rapid Quantification of Donor DNA in the Circulation of Transplant Recipients as a Potential Universal Biomarker of Graft Injury, Clinical chemistry, 59(12):1732-41 (2013).
Benachi et al., Cell-Free DNA Analysis in Maternal Plasma in Cases of Fetal Abnormalities Detected on Ultrasound Examination, Obstetrics & Gynecology, 125(6):1330-7 (2015).
Bethel et al., Fluid phase biopsy for detection and characterization of circulating endothelial cells in myocardial infarction, Physical biology, 11(1):016002 (2014).
Bevilacqua et al., Performance of screening for aneuploidies by cell-free DNA analysis of maternal blood in twin pregnancies, Ultrasound in Obstetrics & Gynecology, 45(1):61-6 (2015).
Bianchi et al., DNA sequencing versus standard prenatal aneuploidy screening, New England Journal of Medicine, 370(9):799-808 (2014).
Bianchi et al., Fetal sex chromosome testing by maternal plasma DNA sequencing: clinical laboratory experience and biology, Obstetrics & Gynecology, 125(2):375-82 (2015).
Bianchi et al., PCR Quantifications of Fetal Cells in Maternal Blood in Normal and Aneuploid Pregnancies, Am. J. Hum. Genet., 61:822-29 (1997).
Bianchi, Invited Editorial Fetal DNA in Maternal Plasma: The Plot Thickens and the Placental Barrier Thins, by The American Society of Human Genetics, 62:763-764 (1998).
Bina-Stein et al., Aurintricarboxylic Acid Is a Nonspecific Enzyme Inhibitor, Department of Chemistry, Yak University, New Haven, Connecticut, 12:191-193 (1975).

(56) References Cited

OTHER PUBLICATIONS

BIOCEPT (BIOC) Announces Patent for Blood Collection and Transport Tube; StreetInsider.com; http://www.streetinsider.com/corporate+news/biocept+(BIOC)+Announces; (2015).
BIOCEPT—Expands Patent Protection for Liquid Biopsy Platform; http://ir.biocept.com/releasedetail.cfm?releaseID=915635 (2015).
BIOCEPT Completing the Answer; http://ir.biocept.com/secfiling.cfm?filingid=1193125-15-16425%cik=1044378. (2015).
Botezatu et al., Genetic Analysis of DNA Excreted in Urine: A New Approach for Detecting Specific Genomic DNA Sequences from Cells Dying in an Organism, Clinical Chemistry, 46(8):1078-1084 (2000).
Brar et al., The fetal fraction of cell-free DNA in maternal plasma is not affected by a priori risk of fetal trisomy, The Journal of Maternal-Fetal & Neonatal Medicine, 26(2):143-5 (2013).
Brown, Effect of Blood Collection and Processing on Radioimmunoassay Results for Apolipoprotein B in Plasma, Clinical Chemistry, 36(9):1662-1666 (1990).
Bruno et al., Use of copy number deletion polymorphisms to assess DNA chimerism, Clinical chemistry, 60(8):1105-14 (2014).
Butler, Genetics and Genomics of Core Short Tandem Repeat Loci Using in Human Identity Testing, Journal of Forensic Science, 51(2):253-265 (2006).
Buysse et al., Reliable noninvasive prenatal testing by massively parallel sequencing of circulating cell-free DNA from maternal plasma processed up to 24h after venipuncture, Clinical biochemistry, 46(18):1783-6 (2013).
Cannas et al., Implications of storing urinary DNA from different populations for molecular analyses, PloS one, 4(9):e6985 (2009).
Carlsson et al, Circulating Tumor Microemboli Diagnostics for Patients with Non-Small-Cell Lung Cancer, Journal of Thoracic Oncology, 9(8):1111-9 (2014).
Chan et al., Hypermethylated RASSFIA in maternal Plasma: A Universal Fetal DNA Marker that Improves the Reliability of Noninvasive Prenatal Diagnosis, Clinical Chemistry, 52(12):2211-2218 (2006).
Cherepanova et al., Immunochemical assay for deoxyribonuclease activity in body fluids, Journal of immunologica methods, 325(1):96-103 (2007).
Chinnapapagari et al., Treatment of maternal blood samples with formaldehyde does not alter the proportion of circulatory fetal nucleic acids (DNA and mRNA) in maternal plasma, Clin Chem., 51(3):652-5 (2005).
Chiu et al., Effects of Blood-Processing Protocols on Fetal and Total DNA Quantification in Maternal Plasma, Clinical Chemistry, 47(9):1607-1613 (2001).
Chudziak et al., Clinical evaluation of a novel microfluidic device for epitope-independent enrichment of circulating tumour cells in patients with small cell lung cancer, The Analyst, 141(2):669-78 (2015).
Chung et al., Detrimental Effect of Formaldehyde on Plasma RNA Detection, Clin. Chem., 51 (6): 1074-6 (2005).
Chung et al., Lack of Dramatic Enrichment of Fetal DNA in Maternal Plasma by Formaldehyde Treatment, Clinical Chemistry, 51(3):655-8 (2005).
Chutkan et al., Quantitative and qualitative preparations of bacterial outer membrane vesicles, Methods Mol. Biol., 966:259-272 (2013).
Clark-Ganheart et al., Use of Cell-Free DNA in the Investigation of Intrauterine Fetal Demise and Miscarriage, Obstetrics & Gynecology, 125(6):1321-9 (2015).
Clinical Applications of Flow Cytometry: Immunophenotyping of Leukemic Cells; Approved Guideline; NCCLS, 18(8) (1998).
Colombo et al., Biogenesis, secretion, and intercellular interactions of exosomes and other extracellular vesicles, Annu. Rev. Cell Dev. Biol., 30:255-89 (2014).
Comas et al., Initial Experience with Non-Invasive Prenatal Testing of Cell-Free DNA for Major Chromosomal Anomalies in a Clinical Setting, The Journal of Maternal-Fetal & Neonatal Medicine, 28(10):1-6 (2014).

Costa et al., Fetal Expressed Gene Analysis in maternal Blood: A New Tool for Noninvasive Study of the Fetus, Clinical Chemistry, 49(6):981-983 (2003).
Curnow et al., Detection of Triploid, Molar, and Vanishing Twin Pregnancies by a Single-Nucleotide Polymorphism-Based Noninvasive Prenatal Test, American Journal of Obstetrics and Gynecology, 212(1):79.e1-9 (2015).
Das et al.,, Effects of a novel cell stabilizing reagent on DNA amplification by PCR as compared to traditional stabilizing reagents, Acta Histochemica; 116(1):55-60 (2014).
Dash et al., Using Noninvasive Prenatal Testing for Aneuploidies in a Developing Country: Lessons Learnt, Journal of Fetal Medicine, 1(3):131-5 (2014).
De Miranda et al., Cyclodextrins and ternary complexes: technology to improve solubility of poorly soluble drugs, Br J. Pharm. Sci., 47(4):665-81 (2011).
Dean et al., Comprehensive human genome amplification using multiple displacement amplification, Pro. Nat. Acad. Sci., 99(8):5261-5266 (2002).
Deatherage et al., Membrane Vesicle Release in Bacteria, Eukaryotes, and Archaea: a Conserved yet Underappreciated Aspect of Microbial Life, Infection and Immunity, 80(6): 1948-1957 (2012).
Denis et al., Efficient Detection of BRAF Mutation in Plasma of Patients after Long-term Storage of Blood in Cell-Free DNA Blood Collection Tubes, Clinical Chemistry, 61(6):886-8 (2015).
Dhallan et al., A noninvasive test for prenatal diagnosis based on fetal DNA present in maternal blood: a preliminary study, The Lancet.; 369 (9560): 474-481 (2007).
Dhallan et al., Methods to Increase the Percentage of Free Fetal DNA Recovered from the Maternal Circulation, JAMA, 291 (9):1114-1119 (2004).
Dharajiya et al., Noninvasive Prenatal Testing Using Cell-Free Fetal DNA in Maternal Plasma, Current Protocols in Human Genetics, 84:8-15 (2015).
Modrek et al., Genome-wide Detection of Alternative Splicing in Expressed Sequences of Human Genes, Nucleic Acid Research, 29(13):2850-2859 (2001).
Motoyama et al., Effect of 2,6-di-O-methyl-alpha-cyclodextrin on hemolysis and morphological change in rabbit's red blood cells, Eur. J. Pharm. Sci., 29(2):111-9 (2006).
Motoyama et al., Involvement of lipid rafts of rabbit red blood cells in morphological changes induced by methylated beta-cyclodextrins, Biol. Pharm. Bull., 32(4):700-5 (2009).
Nair et al., An observational study of circulating tumor cells and (18) F-FDG PET uptake in patients with treatment-naive non-small cell lung cancer, PloS One, 8(7):e67733 (2013).
Nicolaides et al., Validation of targeted sequencing of single-nucleotide polymorphisms for non-invasive prenatal detection of aneuploidy of chromosomes 13, 18, 21, X, and Y, Prenatal Diagnosis, 33(6):575-9 (2013).
Niei et al., Shedding light on the cell biology of extracellular vesicles, Nat. Rev. Mol. Cell Biol., 19(4):213-228 (2018).
Norton et al., Cell-free DNA analysis for noninvasive examination of trisomy, New England Journal of Medicine, 372(17):1589-97 (2015).
Norton et al., Non-Invasive Chromosomal Evaluation (NICE) Study: results of a multicenter prospective cohort study for detection of fetal trisomy 21 and trisomy 18, American Journal of Obstetrics and Gynecology, 207(2):137-e1 (2012).
Notice of Opposition to a European patent dated Apr. 24, 2019, received from the European Patent Office Application No. 02761478.3.
Novaro, American Association for Cancer Research; 93rd Annual Meeting; Apr. 6-10, 2002; San Francisco, California; 43 (2002).
Oh et al., Damage to red blood cells during whole blood storage, J. Trauma Acute Care Surg., 89(2):344-350 (2020).
Ohtani et al., Differential effects of alpha-, beta-and gamma-cyclodextrins on human erythrocytes, Eur. J. Biochem., 186(1-2):17-22 (1989).
Ono et al., Circulating microRNA Biomarkers as Liquid Biopsy for Cancer Patients: Pros and Cons of Current Assays, Journal of clinical medicine, 4(10): 1890-907 (2015).

(56) References Cited

OTHER PUBLICATIONS

Opinion Concerning the Determination of Certain Formaldehyde Releasers in Cosmetic Products. The Scientific Committee on Cosmetic Product and Non-Food Products intended for Consumers, 1-9 (2002).
Palmer et al., Flow cytometric determination of residual white blood cell levels in preserved samples from leukoreduced blood products, Transfusion, 48(1):118-128 (2008).
Pan et al., Cell-free Fetal DNA Levels in Pregnancies Conceived by PIP, Human Reproduction, 20(11):3152-3156 (2005).
Passage from confidential document, Streck, Inc. Cell-Free DNA BCT 510(k) Premarket Notification, Sep. 19, 2012.
Perakis et al., Emerging concepts in liquid biopsies, BMC Med., 15(1):75 (2017).
Persico et al., Cell-free DNA testing in the maternal blood in high-risk pregnancies after first trimester combined screening, Prenatal Diagnosis, 36(3):232-6 (2016).
Pertl et al., Fetal DNA in Maternal Plasma: Emerging Clinical Applications, by The American College of Obstetricians and Gynecologists, 98:483-490 (2001).
Pinzani et al., Circulating nucleic acids in cancer and pregnancy, Methods: A Companion to Methods in Enzymology, 40(4):302-307 (2010).
Punnoose et al., PTEN loss in circulating tumour cells correlates with PTEN loss in fresh tumour tissue from castration-resistant prostate cancer patients, British Journal of Cancer, 113(8):1225-33 (2015).
Puren et al., Laboratory operations, specimen processing, and handling for viral load testing and surveillance, Journal of Infectious Diseases, 201(supp 1):S27-S36 (2010).
Quezada et al., Fetal fraction of cell-free DNA in maternal plasma in the prediction of spontaneous preterm delivery, Ultrasound in Obstetrics & Gynecology, 45(1):101-5 (2015).
Rait et al., Conversions of formaldehyde-modified 2'-deoxyadenosine 5'-monophosphate in conditions modeling formalin-fixed tissue dehydration, J. Histochem Cytochem 54(3):301-310 (2006).
Rajewski et al., Pharmaceutical applications of cyclodextrins. 2. In vivo drug delivery, J. Pharm. Sci., 85 (11 ):1142-1169 (1996).
Ramirez et al., Technical challenges of working with extracellular vesicles, Nanoscale, 10:881-906 (2018).
Raposo et al., Extracellular vesicles: exosomes, microvesicles, and friends, J. Cell Biol., 200(4):373-83 (2013).
Risberg, Establishment of PCR based methods for detection of ctDNA in blood, Thesis submitted for the Master's degree in Biomedicine. Oslo University Hospital, Institute for Cancer Research, Department of Genetics and Oslo and Akershus University College of Applied Sciences, (2013).
Roka et al., Evaluation of the cytotoxicity of (Alpha)-cyclodextrin derivatives on the caco-2 cell line and human erythrocytes, Molecules, 20(11):20269-85 (2015).
Ruiz et al., Limited genomic heterogeneity of circulating melanoma cells in advanced stage patients, Physical Biology, 12(1):016008 (2015).
Rykova et al., Concentrations of Circulating RNA from Healthy Donors and Cancer Patients Estimated by Different Method, Ann. N Y. Acad. Sci., 1075:328-333 (2006).
Salvianti et al., Single circulating tumor cell sequencing as an advanced tool in cancer management, Expert review of molecular diagnostics, 27:1-3 (2015).
Salvianti et al., The pre-analytical phase of the liquid biopsy, N. Biotechnol., 55:19-29 (2020).
Samango-Sprouse et al., SNP-based non-invasive prenatal testing detects sex chromosome aneuploidies with high accuracy, Prenatal diagnosis, 33(7):643-9 (2013).
Samoila et al., Method development and validation for clinical cfDNA extraction from blood, InASCO Annual Meeting Proceedings, 33(15_suppl):e22185 (2015).
Samuel et al., The effect of chorionic villus sampling on the fraction of cell-free fetal DNA in maternal plasma, The Journal of Maternal-Fetal &. Neonatal Medicine, 15:1-4 (2015).

Schatz et al., Preservation of Cell-Free DNA in Stored Blood Samples for the Analysis of the (M) Sept9 Colorectal Cancer Screening Marker Enables Sample Shipment by Mail, Published as a poser at the conference on International federation of clinical chemistry and laboratory medicine Worldlab and EU, Berlin, Germany (2011).
Scheffer et al., Noninvasive fetal blood group genotyping of rhesus D, c, E and of K in alloimmunised pregnant women: evaluation of a 7-year clinical experience, BJOG: An International Journal of Obstetrics & Gynaecology, 118 (11):1340-8 (2011).
Schiavon et al., Analysis of ESR1 mutation in circulating tumor DNA demonstrates evolution during therapy for metastatic breast cancer, Science translational medicine, 7(313):313ra182 (2015).
Sekizawa et al., Apoptosis in Fetal Nucleated Erythrocytes Circulating in Maternal Blood, Prenatal Diagnosis, 20:886-889 (2000).
Seo et al., An Experience of Using the Harmony Test for Genomics-Based Non-invasive Prenatal Testing, Journal of Laboratory Medicine and Quality Assurance, 37(1):44-6 (2015).
Shi et al., Feasibility of noninvasive prenatal testing for common fetal aneuploidies in an early gestational window, Clinica. Chimica. Acta., 439:24-8 (2015).
Sigma-Aldrich, 1-Aza-3,7-dioxabieyclo[3.3.0]octane-5-methanol solution, Available online at <www.sigmaaldrich.com/catalog/product/aldrich/417807?lang=en%region=US>, 5 pages, Accessed Jan. 13, 2014.
Sillence et al., Fetal Sex and RHD Genotyping with Digital PCR Demonstrates Greater Sensitivity than Real-time PCR, Clinical Chemistry, 61(11):1399-407 (2015).
Skidmore et al., Characterization and Use of the Potent Ribonuclease Inhibitor Aurintricarboxylic Acid for the Isolation of RNA from Animal Tissues, Biochem Journal, 263(1): 73-80 (1989).
Slocum et al., Electron-Microscopic Cytochemical Localization of Diamine and polyamine oxidases in Pea and Maize Tissues, Planta., 183:443-450 (1991).
Smid et al., Evaluation of Different Approaches for Fetal DNA Analysis from Maternal Plasma and Nucleated Blood Cells, Technical Briefs, 45(9):1570-1572 (1999).
Smid et al., Quantitative Analysis of Fetal DNA in Maternal Plasma in Pathological Conditions Associated with Placental Abnormalities, Annals New York Academy of Sciences, 951:133-137 (2001).
Smit et al., Semiautomated DNA Mutation Analysis Using a Robotic Workstation and Molecular Beacons, Clinical Chemistry, 47:739-744 (2001).
Irie et al., Cyclodextrin-induced hemolysis and shape changes of human erythrocytes in vitro, J. Pharmacobiodyn, 5 (9):741-744 (1982).
Ishizawa et al., Simple procedure of DNA isolation from human serum, Nucleic Acids Research, 19(20):5792(1991).
Jensen et al., High-throughput massively parallel sequencing for fetal aneuploidy detection from maternal plasma, PloS One, 8(3):e57381 (2013).
Jeon et al., The feasibility study of non-invasive fetal trisomy 18 and detection with semiconductor sequencing platform, PLoS One, 9(10):e110240 (2014).
Jodal et al., Investigation of the hemolytic effect of the cyclodextrin derivatives, Proceedings of the Fourth International Symposium on Cyclodextrins, 421-425, (1988).
Juneau et al., Microarray-based cell-free DNA analysis improves noninvasive prenatal testing, Fetal Diagnosis and Therapy, 36(4):282-6 (2014).
Kadam et al., Quantitative measurement of cell-free plasma DNA and applications for detecting tumor genetic variation and promoter methylation in a clinical setting, The Journal of Molecular Diagnostics, 14(4):346-56 (2012).
Kagan et al., A Sample Preparation and Analysis System for Indentifieation of Circulating Tumor Cells, Journal of Clinical Ligand Assay, 25(1): 104-110 (2002).
Kan Ia et al., Urinary proteases degrade albumin: implications for measurement of albuminuria in stored samples, Annals of Clinical Biochemistry, 47:151-157 (2010).
Kashiwasaki et al., Influence of upper and lower thermoneitral room temperatures (20°C and 25°C) on fasting and post-prandial resting

(56) References Cited

OTHER PUBLICATIONS metabolism under different outdoor temperatures, European Journal of Clinical Nutrition, 44:405-413 (1990).

Katz et al., Mass-Volume Equivalents of Common Chemical Solids, Available at <http://www.chymist.com/Mass-volume%20equivalents.pdf>. 4 pages (2007).

Kelly et al., Circulating microRNA as a biomarker of human growth hormone administration to patients, 6(3):234-8 (2014).

Kidess et al., Mutation profiling of tumor DNA from plasma and tumor tissue of colorectal cancer patients with a novel, high-sensitivity multiplexed mutation detection platform, Oncotarget, 6(4):2549-2561 (2015).

Kirkizlar et al., Detection of Clonal and Subclonal Copy-No. Variants in Cell-Free DNA from Patients with Breast Cancer Using a Massively Multiplexed PCR Methodology, Translational oncology, 8(5):407-16 (2015).

Kreuzer et al., Highly Sensitive and specific Fluorescence Reverse Transcription-PCR Assay for the Pseudogene-free Detection of R,-actin Transcripts as Quantitative Reference, Clinical Chemistry, 45(2):297-300 (1999).

Kwee et al., Measurement of Circulating Cell-Free DNA in Relation to 18F-Fluorocholine PET/CT Imaging in Chemotherapy-Treated Advanced Prostate Cancer, Clinical and Translational Science, 5(1):65-70 (2012).

Lambert-Messerlian et al., Feasibility of using plasma rather than serum in first and second trimester multiple marker Down's syndrome screening, Journal of medical screening, 19(4):164-70 (2012).

Lanman et al., Analytical and clinical validation of a digital sequencing panel for quantitative, highly accurate evaluation of cell-free circulating tumor DNA, PloS one, 10(10):e0140712 (2015).

Latifa et al., Comparative Study of Seven Commercial Kits for Human DNA Extraction from Urine Samples Suitable for DNA Biomarker-Based Public Health Studies, Journal of Biomolecular Techniques, 25(4):96-110 (2014).

LECLERCQ, Interactions between cyclodextrins and cellular components: Towards greener medical applications?, Beilstein J. Org. Chem., 12:2644-62 (2016).

Lee et al., Down Syndrome and Cell-Free Fetal DNA in Archived Maternal Serum, Am. J. Obstet Gynecol, 187(5):1217-21 (2002).

Lee et al., Performance of Momguard, a new non-invasive prenatal testing protocol developed in Korea, Obstetrics & Gynecology Science, 58(5):340-5 (2015).

Lee et al., Survival of Donor Leukocyte Subpopulations in Immunocompetent Transfusion Recipients: Frequent Long-Term Microchimerism in Severe Trauma Patients, Blood, 93:3127-3139 (1999).

Lee et al., The importance of standardization on analyzing circulating RNA, Mol. Diagn. Ther., 21(3):259-268 (2017).

Li, et al., Detection of Paternally Inherited Fetal Point Mutations for 13-Thalassemia Using Size-Fractionated Cell-Free DNA in Maternal Plasma, JAMA., 293(7):843-849 (2005).

Liao et al., Noninvasive prenatal diagnosis of common aneuploidies by semiconductor sequencing, Proceedings of the National Academy of Sciences, 111(20):7415-20 (2014).

Liberti et al., Bioreceptor Fenofluids: Novel Characteristics and their Utility in Medical Applications, Supplied by the British Library, Kluwer Academic Publishers; (1996).

Liu et al., Placental mosaicism for Trisomy 13: a challenge in providing the cell-free fetal DNA testing, Journal of assisted reproduction and genetics, 31(5):589-94 (2014).

Lo et al., Increased Fetal DNA Concentrations in the Plasma of Pregnant Women Carrying Fetuses with Trisomy 21, Clinical Chemistry, 45(10):1747-1751 (1999).

Lo et al., Noninvasive prenatal diagnosis for fetal chromosomal aneuploidies by maternal plasma nucleic acid analysis, Clinical Chemistry, American Association for Clinical Chemistry, 54(3):461-466 (2008).

Lo et al., Presence of Fetal DNA in Maternal Plasma and Serum, The Lancet, 350:485-87 (1997).

Lo et al., Quantitative Analysis of Fetal DNA in Maternal Plasma and Serum: Implications for Noninvasive Prenatal Diagnosis, by The American Society of Human Genetics, 62:768-775 (1998).

Lo, Circulating Nucleic Acids in Plasma and Serum: An Overview, Annals of the New York Academy of Sciences, 945:1-291 (2001).

Lo, Fetal DNA in Maternal Plasma: Biology and Diagnostic Applications, Clinical Chemistry, 46(12): 1903-1906 (2000).

Lo, Fetal Nucleic Acids in Maternal Plasma, Toward the Development of Noninvasive Prenatal Diagnosis of Fetal Chromosomal Aneuploidies, New York Academy of Sciences, 1137:140-143 (2008).

Lo, Introduction: Plasma DNA and Urinary DNA, pp. 261-263, from BRUNS et al. (eds.), Molecular Testing in Laboratory Medicine: Selections from Clinical Chemistry, 1998-2001, AACC Press (2002).

Lo, Molecular Testing of Urine: Catching DNA on the way out, Clinical Chemistry, 46(8):1039-40 (2000).

Loftsson et al., Cyclodextrins in drug delivery, Expert Opin. Drug Deliv., 2:335-351 (2005).

Loftsson et al., Self-association of cyclodextrins and cyclodextrin complexes, J. Pharm. Sci., 93(5):1091-1099 (2004).

Lu et al., Detection and Characterization of Circulating Tumour Cells from Frozen Peripheral Blood Mononuclear Cells, Journal of Circulating Biomarkers, 35(12):1243-6 (2015).

Lutz et al., Release of spectrin-free vesicles from human erythrocytes during ATP depletion. I. Characterization of spectrin-free vesicles, J. Cell Biol., 73(3):548-60 (1977).

Machaca et al., Characterization of apoptosis-like endonuclease activity in avian thymocytes, Biology of the Cell, 76(1):15-22 (1992).

Madabusi et al., RNA extraction for arrays, Methods in Enzymology, 411:1-14 (2006).

Mahammad et al., Cholesterol depletion using methyl-beta-cyclodextrin, Methods in Membrane Lipids, 91-102 (2015).

Makhro et al., Red cell properties after different modes of blood transportation, Front Physiol., 7:288 (2016).

May et al., How Many Species Are There On Earth?, Science, 241:1441-1449 (1988).

Mccullough et al., Non-invasive prenatal chromosomal aneuploidy testing-clinical experience: 100,000 clinical samples, PLoS One, 9(10):e109173 (2014).

MERRIAM-WEBSTER'S Medical Dictionary, p. 606, Springfield, MA: Meniam-Webster Incorporated (1995).

Milde et al., Improved DNA typing of human urine by adding EDTA, Int. J. Legal Med., 112(3):209-210 (1999).

Miller et al., A Simple Salting Out Procedure for Extracting DNA from Human Nucleated Cells, Nucleic Acids Research, 16(3):1215 (1988).

\* cited by examiner

Lymphocyte　　Monocyte　　Neutrophil　　Eosinophil　　Basophil

Red Blood　　Reticulocyte　　Platelet　　nRBC

Lymphocyte　　Monocyte　　Neutrophil　　Eosinophil　　Basophil

Red Blood　　Reticulocyte　　Platelet　　nRBC

SUSPENSION COMPOSITION FOR HEMATOLOGY ANALYSIS CONTROL

CROSS-REFERENCE TO RELATED APPLICATIONS

This application is a Continuation of U.S. application Ser. No. 16/321,747, filed Jan. 29, 2019, which is a U.S. National Phase of PCT/US17/44368, filed Jul. 28, 2017, which claims priority to U.S. Provisional Application No. 62/454,224, filed Feb. 3, 2017 and U.S. Provisional Application No. 62/368,676, filed Jul. 29, 2016, the disclosures of which are incorporated herein by reference in their entirety.

TECHNICAL FIELD

The teachings relates generally to hematology analysis and more particularly to suspension compositions for use in a synthetic control (and resulting control compositions), and a synthetic control, for a semi-automated or automated digital imaging hematology analyzers.

BACKGROUND

For decades, the traditional semi-automated or automated approach to hematology analysis has involved flow based techniques. Blood samples have been aspirated into a hematology analyzer and passed through a detection cell. Relevant characteristics of the blood cells have been measured by light scatter characteristics, electrical characteristics, or otherwise. Based upon detected attributes of the cell, the cell will be classified according to its size and the presence of granular nuclear material. In this manner blood cell differentials can be determined for sub-populations of white blood cells.

In accordance with clinical laboratory standards, performance quality and consistent operation of hematology instruments has employed the use of controls typically have been made from blood cell sources that are treated to preserve the relevant detectable characteristics of the cells. Control manufacturers would use either human or animal blood cells as a blood cell source and process them to achieve and retain a size, density and/or morphology representative of a typical subpopulation of cells, as detected by an instrument detection technique. The respective simulated subpopulations could then be combined in a single control composition, optionally with non-leukocyte blood cell components, such as platelets, reticulated platelets, red blood cells, nucleated red blood cells, reticulocytes, immature reticulocytes, or otherwise.

Examples of teachings addressing approaches to making simulated blood components are described, without limitation, in U.S. Pat. Nos. 4,160,644 and 4,436,821 (teaching simulated platelets); U.S. Pat. No. 6,221,668 (teaching simulated reticulocytes, reticulated platelets and nucleated red blood cells); U.S. Pat. No. 5,432,089 (teaching simulated reticulocytes, and that such simulated reticulocytes may be derived from an anemic animal source); U.S. Pat. No. 6,723,563 (teaching simulated nucleated red blood cells); U.S. Published Application No. 20120308985 (teaching simulated immature reticulocytes); The resulting processed cells after transformation from their natural state, would be suspended in a suspension composition adapted to help preserve the processed cells and enable proper function within an instrument. It was a common practice to suspend the cells in a medium that included lipoprotein. This is described, for example, in U.S. Pat. Nos. 5,270,208 and 5,262,327.

Examples of patents describing the processing of cells from a non-human cell source to form white blood cell subpopulation analogs include U.S. Pat. No. 5,512,485; see also, U.S. Pat. No. 4,704,364. Other examples of teachings of making simulated blood components include U.S. patent application 20030104631; U.S. Pat. Nos. 6,653,063; 6,514, 763; and 5,858,790.

In recent years, efforts have been devoted toward development of semi-automated or automated hematology analyzers that employ digital imaging to analyze patient blood. Assuring instrument integrity and consistency of results remains a challenge for instrument producers and operators. As with traditional semi-automated or automated hematology instruments, the digital imaging instruments require regular quality control testing using one or more convenient and accessible control compositions that yield consistent and reproducible results for a prolonged period of time, and well beyond the useful life of fresh whole blood (e.g., fresh human whole blood).

Due to different detection techniques employed as between traditional semi-automated or automated hematology analyzers and digital imaging hematology analyzers, conventional hematology controls are not necessarily useful with digital imaging hematology analyzers. There is thus a need for new compositions for use in a control for semi-automated or automated digital imaging hematology analyzers. There is a need for a new composition that that provides relatively long term stability of simulated white blood cells (e.g., at least about 3 days, 7 days, 14 days, 30 days, 45 days, 90 days or longer, such as at least about 105 days) when stored at about 2 to about 10° C. There is a need also for a new composition that allows simulated blood cells to be dispensed (e.g., printed) onto a substrate for delivering the simulated blood cells for semi-automated or automated analysis by digital imaging while on the substrate.

SUMMARY

In general, the present teachings address one or more of the above needs by providing a synthetic control composition for a semi-automated or automated digital imaging hematology analyzers. The present teachings address one or more of the above needs by providing a unique suspension composition into which simulated blood cells (e.g., cells that include simulated nucleated blood cells) can be dispersed to form a synthetic control composition for a semi-automated or automated hematology analyzer, and particularly a digital imaging hematology analyzer. In this regard, the present teachings also relate generally to synthetic compositions for assuring quality control of a digital imaging hematology analyzer. The compositions generally will include one or more simulated blood components (which may be derived from one or more processed blood cells) and a suspension composition in accordance with the present teachings. The suspension component is such that stability of the one or more simulated blood components is prolonged significantly as compared with fresh whole blood (e.g., fresh human whole blood).

The teachings herein relate as well to a synthetic control composition that includes, in a unique suspension composition, one or any combination of components for simulating a platelet, a reticulated platelet, a red blood cell, reticulocyte, an immature reticulocyte, a nucleated red blood cell, or a simulated leukocyte population or sub-population and is useful as a quality control composition for a digital imaging hematology analyzer. The synthetic control of the teachings may be useful as a quality control composition for a digital imaging hematology analyzer for analyzing a three-part leukocyte differential, a five-part leukocyte differential, and/or an expanded differential leukocyte analysis (also referred to as an expanded differential white blood cell ("dWBC") analysis).

It can be seen that the synthetic control composition of the teachings may include simulated leukocytes (which may be derived from a human or other source, as discussed herein) provided as an individual subpopulation of leukocytes, and/or a collection of cells capable of differentiation into at least the three and/or the five traditional subpopulations of leukocytes, and/or the simulated leukocytes may be suitable for providing an expanded differential white blood cell ("dWBC") analysis and for total white blood cell count or cell count for any white blood cell sub population.

With attention now to certain other generalities about the present teachings, it can be said that the teachings herein relate generally to a composition adapted for use in assuring quality control of a digital imaging hematology analyzer, including a suspension medium with which at least one simulated nucleated blood component is mixed in a predetermined amount, the suspension medium including a stabilizing agent capable of preserving relevant detectable size and morphology, including detectable nuclear morphological characteristics of the nucleated blood component (including any native nuclear cytoplasm granules), when stored at about 2 to about 10° C. for a period of at least 3 days, 7 days, 14 days, 30 days, 45 days, 90 days or longer, such as at least about 105 days) from the time when the at least one simulated nucleated blood component is initially mixed with the suspension medium.

The control composition in which the suspension composition of the teachings is useful may be a synthetic control composition for simulating one or more components of blood (e.g., human whole blood). The control composition in which the suspension composition of the teachings is useful may be a control composition for simulating cells of a leukocyte population of whole blood (e.g., simulated nucleated blood cells to resemble a leukocyte population or one or more subpopulations). Examples of a leukocyte population of whole blood for use in a control composition with the present suspension composition include a three-part leukocyte population of whole blood (e.g., the control may be to simulate three leukocyte subpopulations of whole blood (namely, neutrophils, lymphocytes and monocytes)), a five-part leukocyte population of whole blood (e.g., the control may be to simulate the traditional five leukocyte subpopulations of whole blood (namely, neutrophils, eosinophils, basophils, lymphocytes, and monocytes)), and/or an extended leukocyte population of whole blood (e.g., the control may include further subpopulations of one or more of the traditional five leukocyte subpopulations of whole blood). An example of another simulated nucleated cell component is a nucleated red blood cell. The suspension composition of the present teachings are also useful to preserve simulated reticulocytes, an immature reticulocyte fraction, or both.

The suspension composition may be employed in a synthetic control composition. The suspension composition may be employed in a synthetic control composition in combination with simulated blood cells (e.g., simulated nucleated blood cells, such as a simulated leukocyte population or sub-population of whole blood and/or a simulated nucleated red blood cell). A simulated leukocyte population or subpopulation of whole blood, for the present teachings, may be derived at least partially, or entirely from leukocytes of human whole blood. The simulated leukocyte population or subpopulation of whole blood may include cells that have been treated in a manner to stabilize their respective cell membranes so that the cells remain substantially intact for a period of time that is longer than cells that are not stabilized. It is possible that all simulated leukocytes of a leukocyte population, including the respective subpopulations, are treated simultaneously (e.g., according to a sequence of one or more partial or complete fixing and lysing steps) to provide the simulated leukocytes.

The suspension composition may be employed in a control composition, in combination with one or more components for simulating a platelet, a reticulated platelet, a red blood cell, reticulocyte, an immature reticulocyte, a nucleated red blood cell, or any combination thereof. For example, the suspension composition may be employed in a control composition in combination with a simulated nucleated red blood cell prepared from a non-human source (e.g., nucleated blood cells of a bird such as a turkey, a fish, or a reptile such as an alligator). For example, it may be possible to provide a source of blood cells suitable for simulating a nucleated red blood cell. Provided blood cells may individually include a membrane enclosing a nucleus and cytoplasm. The membrane may be stabilized to retain the nucleus and cytoplasm. For example, there may be a step of lysing the cells that are provided (e.g., with a solution including saponin) and then fixing with an aldehyde (e.g., glutaraldehyde and/or formaldehyde). It is also possible that no lysing step would be utilized prior to cell fixation.

The amounts of simulated cells in the suspension composition generally are predetermined; for example, the amounts may be known amounts for simulating normal amounts in whole blood and/or abnormal amounts). The suspension composition may be useful in a stand-alone control composition, in which typically a single simulated blood cell component is employed.

In contrast with prior control compositions, the control composition of the present teachings need not necessarily employ a lipoprotein to help assure proper characterization and differentiation of simulated leukocyte cells into their proper subpopulations. The present teachings make use of the recognition that certain stabilization agents can be mixed in a suspension composition with a volume of simulated white blood cells, and for a prolonged period (e.g., at least about 3 days, 7 days, 14 days, 30 days, 45 days, 90 days or longer, such as at least about 105 days, when stored at about 2 to about 10° C.) from the time of mixing, simulated cell components (including the simulated leukocytes) retain relevant detectable size and morphology, including detectable nuclear morphological characteristics of the cell and its nuclear matter, including native nuclear cytoplasm granules. However, it is also possible that lipoprotein may be utilized.

According to one general aspect of the teachings applicable to all embodiments, there is contemplated a suspension composition for simulated leukocytes (e.g., cells that have similar detectable characteristics, such as size, a nucleus morphology and/or morphology of other native nuclear cytoplasm granules, of one or any combination of sub-populations of whole blood) of a hematology analyzer control formulation. The suspension composition is especially useful for a control for a semi-automated or automated digital imaging analyzer. The suspension composition is adapted to retain the detectable characteristics of the simulated blood cells (e.g., simulated nucleated cells such as nucleated leukocytes and/or nucleated red blood cells) over a prolonged period of storage. The suspension composition may include a buffered aqueous solution.

As to all embodiments, the suspension composition may include at least one stabilizing agent (e.g., one that includes at least one polysaccharide, such as (without limitation) a nitrogen-containing polysaccharide) having a polymerization degree ranging from greater than one to about 100). The at least one stabilizing agent may be present in an amount sufficient for preserving stability of the detectable size and morphological characteristics of the simulated simulated blood cells (e.g., simulated nucleated cells such as nucleated leukocytes and/or nucleated red blood cells) for a period of at least about 3 days (e.g., at least about 3 days, 7 days, 14 days, 30 days, 45 days, 90 days or longer, such as at least about 105 days) when stored at about 2 to about 10° C.), from the time of suspending the simulated cells.

Generally, the suspension composition may be adapted (as to all embodiments) for use in digital imaging hematology instrument that creates and analyzes an image, such as by applying one or more automated or semi-automated analytical techniques, after a sample has been dispensed onto a substrate. For instance, upon mixing the suspension composition with the simulated leukocytes, the resulting mixture is capable of dispensing through a nozzle for delivery to a substrate for analysis by a digital imaging hematology analyzer. The suspension composition may be adapted, upon mixing with the simulated blood cells (e.g., simulated nucleated cells such as nucleated leukocytes and/or nucleated red blood cells), for dispensing through a nozzle (e.g., a capillary or other tube) for delivery by printing to a transparent substrate (e.g., a glass or polymeric slide) and subsequent analysis by a semi-automated or automated digital imaging hematology analyzer, without any material damage (e.g., damage to excess of five percent (10%) by number of total simulated cells) to the simulated cells. It is possible that the control composition may be delivered into a cassette or cartridge device which may provide digital images for identifying cell populations.

In general, as to all embodiments, the aqueous buffered solution of the suspension composition may include at least one buffering agent.

The aqueous buffered solution may include at least one dispersion agent for reducing aggregation of the simulated blood cells (e.g., simulated nucleated cells such as nucleated leukocytes and/or nucleated red blood cells) as compared with the aqueous buffered solution without the dispersion agent.

The suspension composition may have a pH ranging from about 6 to about 8.

The at least one stabilizing agent may include an organic compound having at least one glycosidic linkage. The at least one stabilizing agent may include a compound that includes an amine moiety and a carbohydrate (e.g., glucose and/or dextrose) moiety.

The at least one stabilizing agent may include at least one amino polysaccharide having a polymerization degree ranging from greater than one to about 100 (e.g., from greater than about 5 to about 40). The at least one stabilizing agent may include or consist of an oligosaccharide (or a derivative of an oligosaccharide) having a weight average molecular weight (measured by high performance liquid chromatography, which may be further verified by comparison with commercially available standards)) from about 100 to about 15,000 daltons (Da), from about 250 to about 10,000 Da, about or even about 1000 to about 3000 Da.

The at least one stabilizing agent may include a glucosamine, or a derivative thereof. It may include one or more of a chitosan and/or chitin, a salt of a chitosan and/or chitin, and/or some other derivative of a chitosan and/or chitin.

The at least one stabilizing agent may be in a polymeric form. The at least one stabilizing agent may be in a salt form (e.g., a salt of a chitosan and/or chitin). Illustrative salts include one or any combination of a citrate, a malate, a lactate, an acetate, a formate, a glyoxylate, a pyruvate, an ascorbate or glycolate.

Generally applicable to all embodiments, the at least one stabilizing agent may be present in an amount up to about ten percent (15%) (e.g., up to about ten percent (10%) or about seven percent (7%)) of the suspension composition. The at least one stabilizing agent may be present in an amount up to about ten percent (10%) (e.g., up to about seven percent (7%) or about five percent (5%) of a resulting control composition admixture including the suspension composition and the simulated cells.

Unlike certain control compositions of the prior art, the suspension composition and any resulting control composition employing the suspension composition of the general teachings herein may be substantially free of any added lipid (e.g., lipoprotein), any glycoprotein or both.

The teachings herein also contemplate a blood control composition (e.g., leukocyte and/or nucleated red blood cell-containing control) composition adapted for use in a semi-automated or automated digital imaging hematology analyzer comprising the suspension composition of the teachings, as well as the use of the composition. For instance, the teachings envision a method of using the suspension composition including a step of dispensing the suspension composition onto a substrate, and at least partially evaporating water from the aqueous buffered suspension composition. Thereafter, a digital image can be made. For instance, when cells are deposited onto a substrate with the suspension composition, a digital image may be made of the cells. The image may be analyzed. For instance the image may be analyzed by a computer implemented technique.

Other benefits and advantages of the teachings will be understood upon review of the remaining teachings, which provide additional details.

DETAILED DESCRIPTION

Figure 1:
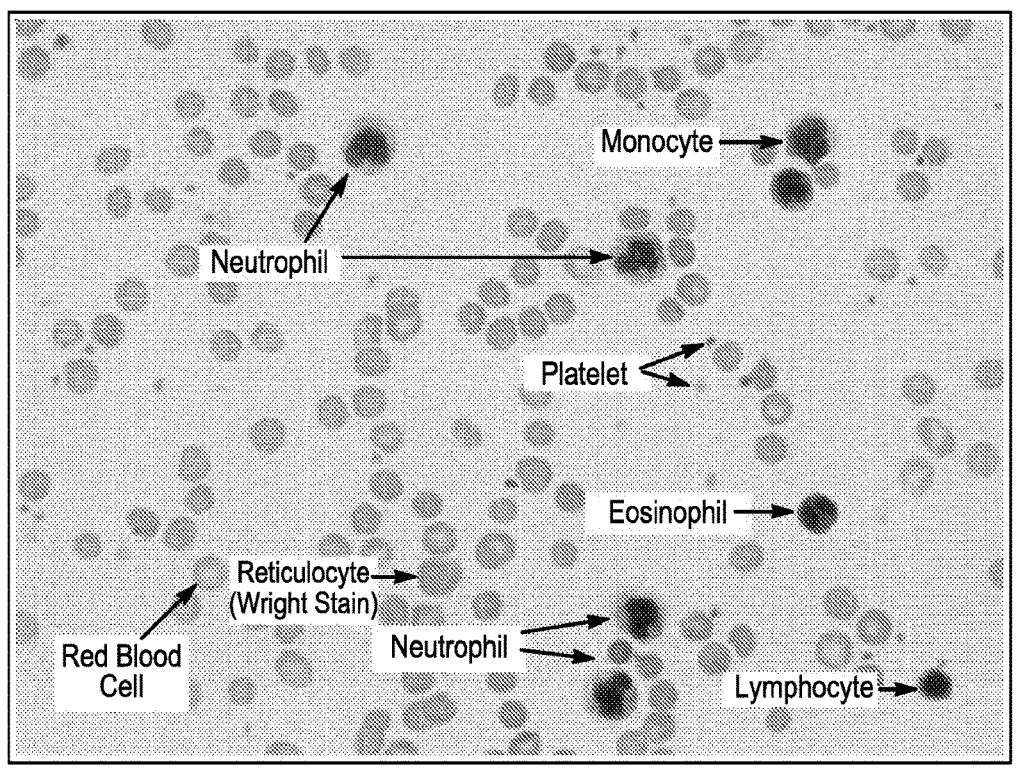
FIG. 1 is a micrograph illustrating cells of fresh human whole blood, as viewed by optical microscopy (oil immersion lens at 100×), in a form as would be detectable by a digital imaging hematology analyzer.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

This application claims the benefit of the filing date of U.S. Provisional Application Ser. Nos. 62/368,676, filed Jul. 29, 2016 and 62/454,224, filed Feb. 3, 2017, the contents of these applications being hereby incorporated by reference herein for all purposes.

Unless otherwise stated, concentrations are expressed in weight/volume percentages (w/v%). Thus, to illustrate, 1% of an ingredient in a liquid medium would refer to 1 gram of the ingredient in 100 milliliters of the liquid. Unless otherwise stated, references herein to "whole blood" and/or "blood cells", include human whole blood. Though the teachings herein are particularly applicable in human whole blood analysis, they are not so limited, and may have application in veterinary applications as well. The phrase "digital imaging hematology instrument" refers to automated hematology analyzers of an automated or semi-automated type that employ computer implemented analysis of a digital image of a sample (e.g., a computer may analyze the sample to ascertain cell size, cell morphology, count cells, and /or classify cells, and may also output resulting data and/or images for independent human analysis). An example of such analysis technology is exemplified by the Cobas m511™, by Roche Diagnostics, which employs what is referred to as Bloodhound™ analysis technology. It is believed that such technology is described in one or more of U.S. Patent Application Nos. 20090269799; 20110014645; 20130070077; 20130077085; and WO/2013/016038.

The phrase "detectable characteristics" refers to one or more characteristics (e.g., a physical characteristic, such as size and/or morphology) that are detectable by a hematology instrument, whether a digital imaging hematology instrument or otherwise.

In general, the teachings herein contemplates a suspension composition for preserving the stability of simulated blood cells of a hematology control composition. The teachings more particularly contemplates a suspension composition for preserving the stability of simulated blood cells, so that the cells exhibit and retain relevant detectable characteristics, such as size, and/or morphology. One particular advantage of the teachings is the ability of the suspension composition to preserve the stability nuclear morphological characteristics (including morphology of native nuclear cytoplasm granules) for a period substantially longer than fresh human whole blood. The suspension composition teachings are useful to prepare a suspension of a control composition for assuring quality of a hematology analyzer (e.g., a digital imaging hematology analyzer).

In general, the suspension composition is useful for and may be part of a control composition that include the suspension and simulated blood cells (e.g., simulated nucleated cells such as nucleated leukocytes and/or nucleated red blood cells). Such control composition and methods of using the controls are part of the teachings herein as well.

Determination of whether relevant detectable characteristics are retained can be done by optical examination (e.g., including the use of a digital imaging device for outputting an image) of a statistically significant number of samples, with analysis to identify material deviations from native morphological attributes of the type of cell under consideration. Indicators of material deviations can employ optical means to identify. It may include a comparative study of a sample with data (which may include images) about known characteristics of the sample material in its normal freshly prepared state. The skilled person likewise would recognize that relevant detectable characteristics have not been attained, or are no longer retained (e.g., a stability period has been exceeded) when a sample intended yields cell counts that deviate from the intended values in excess of at least ten percent (10%), or there is some other evidence indicative of an inability to differentiate cells; when nucleated blood cells present identifiable surface cracks in images at a magnification of at least 100× (e.g., when viewed by optical microscopy with an oil immersion lens); when cellular cytoplasm appears de-granulated and not readily identifiable in images at a magnification of at least 100× (e.g., when viewed by optical microscopy with an oil immersion lens), and/or when one or more nuclei sizes deviate from their normal well known sizes.

It should thus be recognized, that the phrase "simulated blood cells" is used herein not only to refers to cells from a non-human source that are adapted to resemble blood cells from a human (or those of another species) in relevant detectable characteristics by a hematology analyzer (e.g., a digital imaging analyzer). The phrase "simulated blood cells" also refers to blood cells that are true human blood cells. Thus, a source of simulated white blood cells, in accordance with the teachings herein may be human white blood cells. Moreover, any of the simulated blood cells that are suspended in the suspension composition may be cells derived from human whole blood and/or non-human whole blood source (e.g., blood from a source selected from avian blood, fish blood, reptilian blood, mammalian blood or otherwise.

The suspension composition may be employed in a control composition, alone or in combination with simulated blood cells, which may include simulated leukocytes or other simulated cell components of whole blood (e.g., simulated nucleated cells such as nucleated leukocytes and/or nucleated red blood cells). A simulated leukocyte population or subpopulation of whole blood may be derived at least partially, or entirely from leukocytes of human whole blood. The simulated leukocyte population or subpopulation of whole blood may include cells that have been treated in a manner to stabilize their respective cell membranes so that the cells remain substantially intact for a period of time that is longer than cells that are unstabilized. It is possible that all simulated leukocytes of a leukocyte population, including the respective subpopulations, are treated simultaneously to provide the simulated leukocytes. For example, a source of leukocytes (e.g., a leukocyte pack from a blood bank) may be provided and the leukocytes contacted with a stabilizer to partially stabilize the cell membranes of the leukocytes. The source is then lysed to eliminate red blood cells. The leukocytes may then be further stabilized prior to combining them with the suspension.

In general, the present teachings provide a unique suspension composition into which simulated blood cells can be dispersed to form a control composition. In contrast with prior control compositions, the control composition of the present teachings need not necessarily employ a lipoprotein to help assure proper characterization of simulated leukocytes and/or differentiation of the simulated blood cells into their proper subpopulations.

The present teachings make use of the recognition that certain stabilization agents can be mixed in a suspension composition with a volume of simulated blood cells (e.g., for simulation one or more subpopulations of white blood cells), and for a prolonged stability period (e.g., at least about 3, at least about 7, at least about 14, at least about 30, at least about 45, at least about 90 days or longer, e.g., at least about 105 days, while maintained at a temperature of about 2 to about 10° C.) from time of mixing, the simulated blood cells (e.g., simulated leukocytes, and any other simulated blood cell component such as a nucleated red blood cell component) retain relevant detectable characteristics such as size and/or nuclear morphological characteristics (including morphology of native nuclear cytoplasm granules).

According to one general aspect of the teachings applicable to all embodiments, there is contemplated a suspension composition for simulated blood cells of a hematology analyzer control formulation, which may be a digital imaging hematology analyzer. The simulated blood cells may be cells from a suitable source that have been processed to attain and/or preserve characteristics detectable by a hematology analyzer, such as a digital imaging hematology analyzer. For instance, the characteristics that are attained and/or preserved may be size, a nucleus morphology and/or morphology of other nuclear cytoplasm granules.

The teachings herein have application for suspending and preserving stability of simulated blood components (e.g., blood cells) in a control composition. For example, the teachings have application for suspending and preserving stability of simulated leukocytes of a control composition. The simulated leukocytes (which may be derived from a human or other source, as discussed above) may be provided as an individual subpopulation of leukocytes, and/or a collection of cells capable of differentiation into at least the three and/or the five traditional subpopulations of leukocytes. The simulated leukocytes may be suitable for providing an expanded differential white blood cell ("dWBC") analysis.

A control in accordance with the teachings for an expanded dWBC analysis may include (e.g., in addition to the traditional 3 or 5 subpopulations) components that simulate one or more cell populations that may include blasts, immature granulocytes, atypical lymphocytes (types I, II and III), myeloid precursors (myeloblast, promyelocyte, myelocyte and metamyelocyte) and or lymphocyte subsets (T-Cells and B-Cells).

The suspension composition is adapted to retain the detectable characteristics of the simulated blood cells (e.g., white blood cells) over a prolonged period of storage. For example, the suspension composition (whether used for simulated white blood cells and/or other blood cells is formulated to preserve relevant detectable characteristics, such as size and/or nuclear morphological characteristics (including morphology of native nuclear cytoplasm granules) of the simulated blood cells, fora prolonged stability period (e.g., at least about 3, at least about 7, at least about 14, at least about 30, at least about 45, at least about 90 days or longer, e.g., at least about 105 days) when stored at about 2 to about 10° C. from time of mixing with the suspension composition.

Throughout the prolonged stability period, the nucleated cells (e.g., the simulated leukocytes (and/or any other simulated cell components such as simulated nucleated red blood cells) will resemble to a detector of a hematology analyzer, and particularly a digital imaging hematology analyzer (e.g., without limitation, a COBAS m511™ analyzer from Roche) the blood cell it is intended to simulate. Thus, the simulated blood cell is capable of being subjected to sample processing by a digital imaging hematology instrument, during which the cell may be deposited on a slide (such as by a printing operation), stained, and imaged in a manner suitable for computer implemented image analysis.

The suspension composition may be isotonic. The suspension composition may include a buffered aqueous solution. The suspension composition may include a mixture of cell stabilizers. The suspension composition may include an antimicrobial. The suspension composition may include one or more agents for maintaining a predetermined pH.

As to all embodiments, the suspension composition may include at least one stabilizing agent (e.g., one that includes at least one polysaccharide having a polymerization degree ranging from greater than one to about 100, such as (without limitation) a nitrogen containing polysaccharide). The at least one stabilizing agent may be present in an amount sufficient for preserving stability of the detectable morphological characteristics of the white blood cells for a period of at least about 3 days (e.g., at least about 7, at least about 14, at least about 30, at least about 45, at least about 90 days or longer, e.g., at least about 105 days), after being stored during such period at about 2 to about 10° C., upon suspending the simulated white blood cells.

Generally, the suspension composition may be adapted (as to all embodiments) for use in digital imaging hematology instrument that creates and analyzes by a computer implemented technique an image of a sample that has been dispensed onto a substrate. For instance, upon mixing the suspension composition with the simulated leukocytes, the resulting mixture is capable of dispensing through a nozzle for delivery to a substrate for analysis by a digital imaging hematology analyzer. The suspension composition may be adapted, upon mixing with the simulated white blood cells, for dispensing through a nozzle (e.g., a capillary or other tube) for delivery by printing to a transparent substrate (e.g., a glass or polymeric slide) and subsequent analysis by a digital imaging hematology analyzer, without any material damage (e.g., damage to excess of five percent (10%) by number of total simulated blood cells) to the simulated blood cells.

The at least one stabilizing agent may be present (as to all embodiments) in an amount sufficient for preserving stability of the detectable morphological characteristics of the white blood cells for a period of at least 30 days, after being stored during such period at about 2 to about 10° C., upon suspending the white blood cells. More specifically, as applicable to the teachings in general, the at least one stabilizing agent may function to retain intact relevant detectable characteristics such as size and/or nuclear morphological characteristics (including morphology of native nuclear cytoplasm granules) of one or more of any simulated nucleated blood cell component of a control composition. Thus, the size and shape of a nucleus of the simulated blood cell be preserved substantially as it would be in its native state in fresh whole blood. It is also possible that the size, shape and/or amount of other nuclear matter (e.g., cytoplasm) may be preserved substantially as it would be in its native state in fresh whole blood.

The at least one stabilizing agent may be part of a stabilization mixture. Such stabilization mixture may include two, three, four, five or more ingredients. Such stabilization mixture may include twelve, ten, eight or fewer ingredients. The ingredients of the stabilization mixture may be in an amount effective for stabilizing one or more aspects of a simulated blood cell (e.g., a simulated leukocyte or any other simulated blood cell component, such as a platelet, a reticulated platelet, a red blood cell, reticulocyte, an immature reticulocyte, a nucleated red blood cell, or any combination thereof). For example, one or more of the ingredients may be for stabilizing a membrane, for stabilizing nuclear material, for stabilizing a nucleic acid, for stabilizing cytoplasm, or otherwise).

In general, as to all embodiments, the aqueous buffered solution of the suspension composition may include at least one buffering agent. It may include at least one antimicrobial. The aqueous buffered solution may include at least one dispersion agent for reducing aggregation of the simulated white blood cells as compared with the aqueous buffered solution without the dispersion agent. The suspension composition may have a pH ranging from about 6 to about 8.

In general, as to all embodiments, with regard to the at least one stabilizing agent, it may include at least one polysaccharide, such as is set forth in the following. The at least one stabilizing agent may be a nitrogen-containing polysaccharide. The at least one stabilizing agent may be a derivative of glucose. It may include one or more glucose moieties. However, the at least one stabilizing agent may be substantially free of simple glucose (i.e., that represented by the formula $C_6H_{12}O_6$); that is, the suspension medium may include less than about 10%, or less than about 5% glucose of the suspension medium.

For example, the at least one stabilizing agent may include at least one amino polysaccharide having a polymerization degree ranging from greater than one to about 100 (e.g., from greater than about 5 to about 40). The at least one stabilizing agent may include or consist of an oligosaccharide (or a derivative of an oligosaccharide) having a weight average molecular weight (measured by high performance liquid chromatography, which may be further verified by comparison with commercially available standards)) from about 250 to about 10,000 daltons (Da), from about 250 to about 10,000 Da, or even about 1000 to about 3000 Da.

The at least one stabilizing agent may include a glucosamine, or a derivative thereof. It may include one or more of a chitosan, a salt of a chitosan or some other derivative of a chitosan.

The at least one stabilizing agent may be in a polymeric form. The at least one stabilizing agent may be in a salt form (e.g., a salt of a chitosan). Illustrative salts include one or any combination of a citrate, a malate, a lactate, an acetate, a formate, a glyoxylate, a pyruvate, an ascorbate or glycolate.

By way of example, the at least one stabilizing agent may include one or any combination of D-(+)-glucosamine, N-acetyl-D-glucosamine, chitosan acetate, chitosan lactate, chitosan oligosaccharide, chitin, carboxyl methyl chitosan, a derivative of any of these listed agents, or any combination of the same.

Generally applicable to all embodiments, the at least one stabilizing agent may be present in an amount up to about fifteen percent (15%) (e.g., up to about ten percent (10%) or about seven per cent (7%)) about ten percent (10%) or about seven per cent (7%)) of the suspension composition. The at least one stabilizing agent may be present in an amount up to about ten percent (10%) (e.g., up to about seven percent (7%) or about five percent (5%) of a resulting control composition admixture including the suspension composition and the white blood cells. Generally applicable to all embodiments, the at least one stabilizing agent along with any other ingredients functional for preserving stability of a simulated blood cell (i.e., the total functional ingredients of the stabilizing mixture), may be present in amount up to about twenty five percent (25%); twenty two percent (22%); or about eighteen (18%) (e.g., up to about fifteen percent (15%) or about ten per cent (10%)) of the suspension composition. The total functional ingredients of the stabilizing mixture may be present in an amount of at least about one percent (1%) (e.g., at least about seven percent (3%) or about five percent (5%)) of a resulting control composition admixture including the suspension composition and the white blood cells.

Unlike certain control compositions of the prior art, the suspension composition and any resulting control composition employing the suspension composition of the general teachings herein may be substantially free of any added lipid (e.g., lipoprotein), any glycoprotein or both. For example, it may have less than 0.3 percent (e.g., less than about 0.1 percent) of a lipid and/or glycoprotein. Alternatively stated, to the extent any lipid (e.g., lipoprotein), any glycoprotein or both are employed in a suspension composition in accordance with the present teachings, such lipid (e.g., lipoprotein), glycoprotein or both is employed in an insufficient amount to materially alter the stability characteristics of any of the resulting blood components of the resulting control composition during the stability period. For instance, the amount is an amount at which detectable nuclear morphological characteristics of the nucleated blood component (including any native nuclear cytoplasm granules) exhibit less than a 10%, or even less than a 5%, variation in detected cell counts when analyzed by a digital hematology analyzer as compared with a control having no such lipid (e.g., lipoprotein), glycoprotein or both.

Though the suspension composition may be substantially free of any lipoprotein, it may optionally include lipoprotein. For instance, it may include a lipoprotein in a suitable amount for assuring proper differentiation of white blood cells added to the suspension composition. The suspension composition may include, or it may be free of an antioxidant (e.g., in an amount sufficient to prevent cell lysis during the stability period of a control in which the suspension composition is used).

The suspension composition may include at least one cellular aggregation inhibition ingredient, or may be free of any cellular aggregation inhibition ingredient. The suspension composition may include a surfactant (e.g., in an amount sufficient to effect a surface energy characteristic of any of the simulated blood cells), or it may be free of any surfactant. Examples of surfactants can be found in U.S. Pat. No. 5,250,438, (see, e.g., column 3), incorporated by reference.

In general, as to all embodiments, the aqueous buffered solution of the suspension composition may include at least one buffering agent. For example, it may be zwitterionic buffering agent. The at least one buffering agent may include a sulfonic acid moiety. The buffering agent may be selected from one or any combination of 3-Morpholinopropane-1-sulfonic acid (MOPS); 2-[[1,3-dihydroxy-2-(hydroxymethyl)propan-2-yl]amino]ethanesulfonic acid (TES); or 2-[4-(2-hydroxyethyl)piperazin-1-yl]ethanesulfonic acid (HEPES). The at least one buffering agent may be present in an amount of up to about 7 percent, up to about 5 percent or up to about 3 percent of the suspension composition. The at least one buffering agent may be present in an amount of greater than about 0.5 percent or greater than about 1 percent of the suspension composition.

The suspension composition may include at least one antimicrobial. The at least one antimicrobial may be part of the aqueous buffered solution or a separate ingredient. The at least one antimicrobial may be organic or inorganic. The at least one antimicrobial may include a biocide, a microbe growth inhibitor, and/or a microbe reproduction inhibitor. The at least one anti-microbial may be a bacteriostatic ingredient (e.g., one that inhibits cytochrome oxidase in gram negative bacteria). The at least one anti-microbial may be an anti-fungal ingredient. The at least one anti-microbial may be an anti-yeast ingredient. Examples of suitable antimicrobials include one or more antimicrobials selected from chloramphenicol, sodium azide, neomycin sulfate, Rifampicin minocycline, ciproflaxin, doxycycline, sulfasalazine or the like. The at least one antimicrobial may be present in an amount of up to about 5%, up to about 3% or up to about1% percent of the suspension composition.

The suspension composition may have a pH ranging from about 6 to about 8. Suitable amounts of neutralizing agents may be employed in the suspension composition. For example, a relatively mild acid such and/or a relatively mild base such as sodium hydroxide may be titrated into the suspension composition as needed to achieve the desired pH level.

As gleaned from the above, it is envisioned that the suspension composition may include one or more inorganic compounds. The inorganic compound may include a metallic atom or cation, such as an atom or cation of an alkali metal, an alkaline earth metal, a transition metal, or any combination thereof. For example, it is possible that the resulting suspension composition will have one or more metal atoms or cations selected from magnesium (Mg), calcium (Ca), sodium (Na), potassium (K), lithium (Li), iron (Fe), or otherwise. The amount of the metal atoms or cations may be quantified as a proportion relative to the polysaccharide of the suspension composition. For example, the amount of atoms or cations by weight relative to the polysaccharide may range from about 0.1:1 to about 2:1 (e.g., about 0.3:1 to about 1:1).

To the extent not covered in the above, the suspension composition may include one or more other ingredients, including one or any combination of an alcohol, a surfactant; a protease inhibitor; serum albumin protein; an anticoagulant (e.g., ethylenediaminetetraacetic acid "EDTA"), a gelatin, an aldehyde (e.g., glutaraldehyde and/or formaldehyde), a polyol (e.g., polyethylene glycol), a cellulosic agent, an antioxidant, a protein, a blood serum fraction, plasma, amino acid precursor, a cholesterol (e.g., a lipoprotein), or any combination of the above.

In general, water used for the aqueous compositions herein may be distilled water, deionized water, filtered water, any combination thereof or another source of water that is free of detectable amounts of contaminants that would materially impact performance of the suspension composition.

The teachings herein also contemplate a blood control composition (e.g., a white blood cell control composition) adapted for use in a digital imaging hematology analyzer comprising the suspension composition of the teachings, as well as the use of the composition. For instance, the teachings envision a method of using the suspension composition including a step of dispensing the suspension composition onto a substrate, and at least partially evaporating water from the aqueous buffered suspension composition. Thereafter, a digital image can be made. For instance, when cells are deposited onto a substrate with the suspension composition, a digital image may be made of the cells. The image may be analyzed.

Turning now to the accompanying FIGS. 1, 2, 3a, 3b, 4a, 4b, and 5 various benefits and advantages of the teachings can be further gleaned. Except as otherwise described, the images are believed representative of compositions that would result using a suspension medium, generally, of the present teachings, and particularly the suspension medium described below in Example 1. The images are believed representative of compositions that would result from simulated cell components that include simulated leukocytes, wherein the simulated leukocytes are derived from human blood cells. Similar results are also expected when the simulated leukocytes are derived from non-human blood cells.

FIG. 1 is a micrograph illustrating cells of fresh human whole blood, as viewed by optical microscopy (oil immersion lens at 100×), in a form as would be detectable by a digital imaging hematology analyzer. Examples of the cellular components are labeled for reference purposes. Upon draw, the respective cellular components of the fresh human whole blood substantially identically resemble the cellular components as would be circulating within person from whom the blood was drawn.

Figure 2:
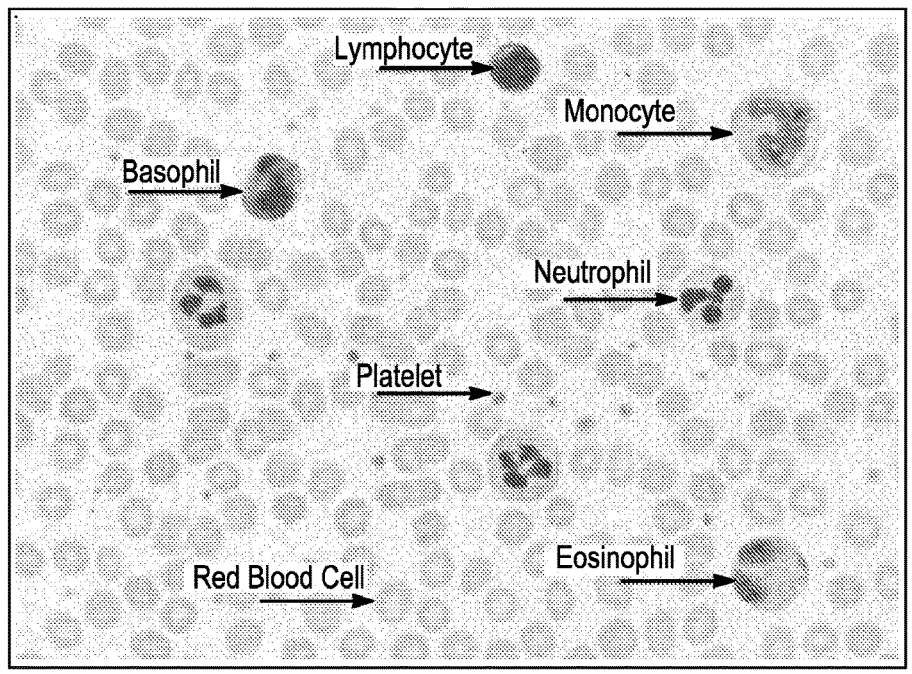
FIG. 2 is a micrograph illustrating simulated leukocytes cells in a freshly prepared suspension composition of the present teachings as viewed by optical microscopy (oil immersion lens at 100×), in a form as would be analyzed by a digital imaging hematology analyzer.

FIG. 2 is a micrograph illustrating simulated leukocytes cells in a freshly prepared suspension composition of the present teachings as viewed by optical microscopy (oil immersion lens at 100×), in a form as would be detectable by a digital imaging hematology analyzer. As seen from FIG. 2, there is substantial identify as between the simulated cellular components and the cellular components of FIG. 1. In accordance with the teachings in general, the suspension medium of the present teachings is particularly attractive for us with simulated blood cell components (e.g., at least simulated leukocytes, such as stabilized human leukocytes).

Figure 3A:
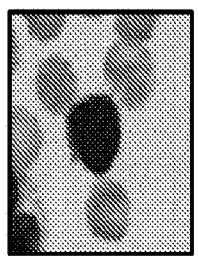
FIG. 3a is an enlarged micrograph illustrating respective examples of simulate leukocyte subpopulation cells and other simulated cell components in a suspension composition of the present teachings as viewed by optical microscopy (oil immersion lens at 100×), in a form as would be analyzed by a digital imaging hematology analyzer.
Figure 3A:
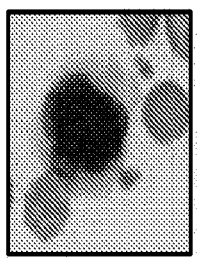
Figure 3A:
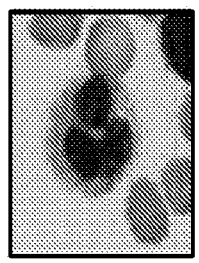
Figure 3A:
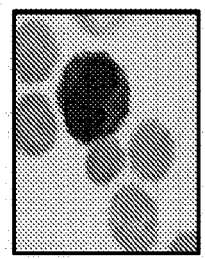
Figure 3A:
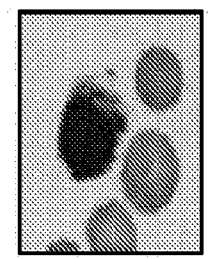
Figure 3A:
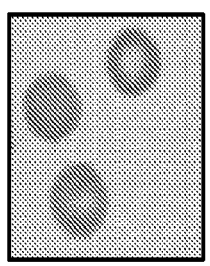
Figure 3A:
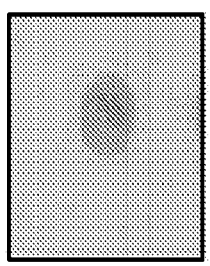
Figure 3A:
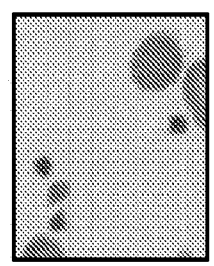
Figure 3A:
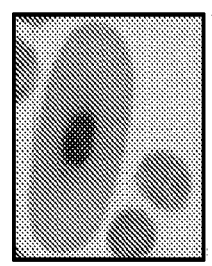
Figure 3B:
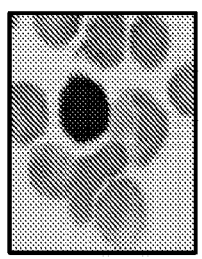
FIG. 3b is an enlarged micrograph illustrating respective examples of leukocyte subpopulation cells and other simulated cell components after storage at about 2 to about 10° C. for 105 days in a suspension composition of the present teachings as viewed by optical microscopy (oil immersion lens at 100×), in a form as would be analyzed by a digital imaging hematology analyzer.
Figure 3B:
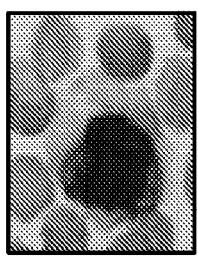
Figure 3B:
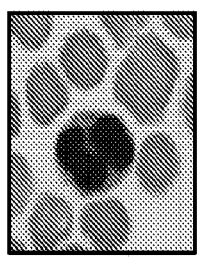
Figure 3B:
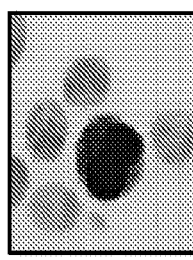
Figure 3B:
Figure 3B:
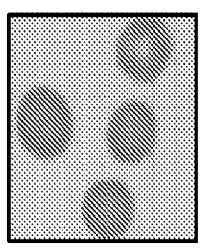
Figure 3B:
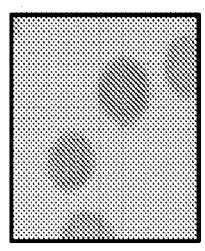
Figure 3B:
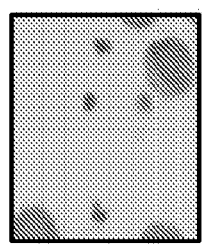
Figure 3B:
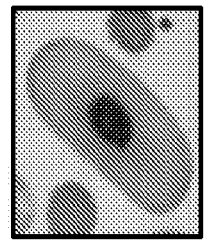

FIGS. 3a and 3b are included for comparison.

FIG. 3a is an enlarged micrograph illustrating respective examples of simulated leukocyte subpopulation cells and other simulated cell components in a suspension composition of the present teachings, the components and suspension composition being freshly prepared, as viewed by optical microscopy (oil immersion lens at 100×), in a form as would be detectable by a digital imaging hematology analyzer.

For comparison with FIG. 3a, FIG. 3b is an enlarged micrograph illustrating respective examples of leukocyte subpopulation cells and other simulated cell components after storage at about 2 to about 10° C. for 105 days in a suspension composition of the present teachings as viewed by optical microscopy (oil immersion lens at 100×), in a form as would be detectable by a digital imaging hematology analyzer. The image illustrates that as between the freshly prepared materials of FIG. 3a and those of FIG. 3b, there are indistinguishable differences if any. As expected in general for the teachings herein, the nucleic subject matter within the granulated cells, in particular, remains intact through a useful life orders of magnitude longer than it would if not suspending in the suspension medium of the teachings (e.g., at least 105 days).

Figure 4A:
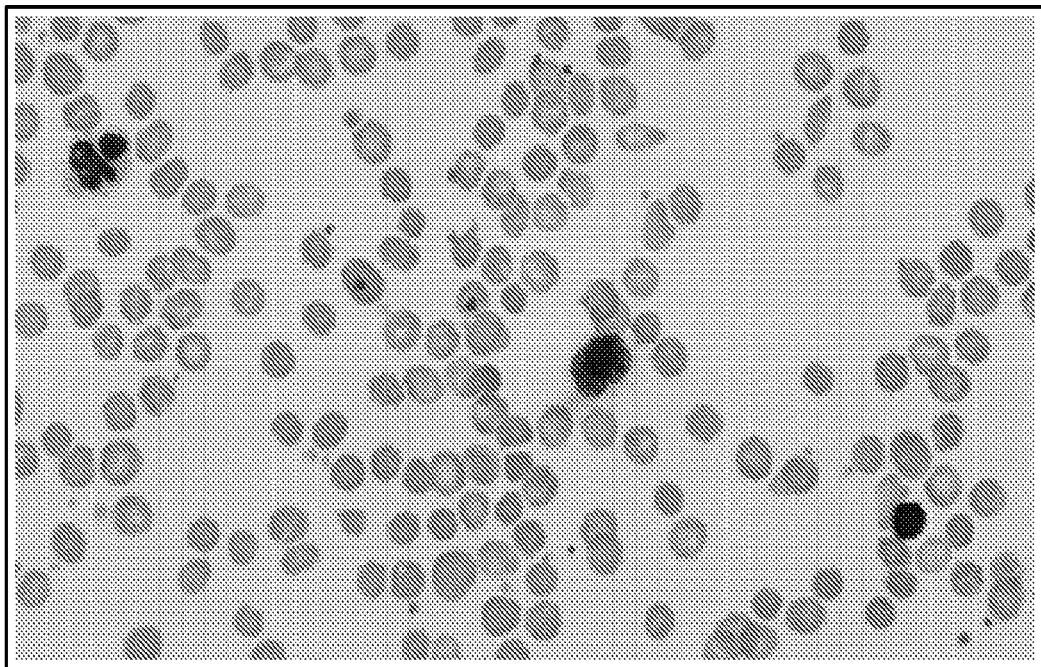
FIG. 4a is a micrograph to illustrate an example of simulated leukocyte cells in a suspension medium including a stabilizing agent of the present teachings after about three weeks as viewed by optical microscopy (oil immersion lens at 100×), in a form as would be analyzed by a digital imaging hematology analyzer.
Figure 4B:
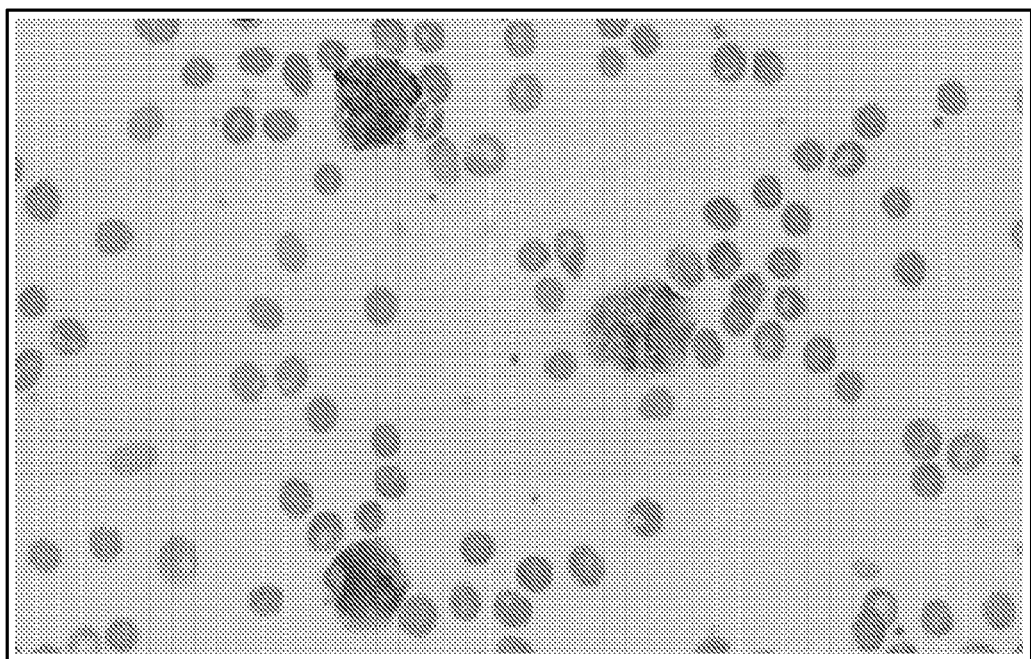
FIG. 4b is a micrograph to illustrate an example of simulated leukocyte cells of the present teachings in a suspension medium as in FIG. 4a, but absent any stabilizing agent of FIG. 4a after about three weeks as viewed by optical microscopy (oil immersion lens at 100×), in a form as would be analyzed by a digital imaging hematology analyzer.

FIGS. 4a and 4b are included for comparison.

FIG. 4a is a micrograph to illustrate an example of simulated leukocyte cells in a suspension medium including a stabilizing agent (e.g., a polysaccharide, such as chitosan or another glucosamine, having a polymerization degree ranging from greater than one to about 100) of the present teachings after about three weeks as viewed by optical microscopy (oil immersion lens at 100×), in a form as would be detectable by a digital imaging hematology analyzer. Consistent with the illustrations of the teachings in FIGS. 2, 3a and 3b, the cellular components resemble those of fresh whole blood (e.g., fresh human whole blood), as seen in FIG. 1.

FIG. 4b is a micrograph to illustrate an example of simulated leukocyte cells of the present teachings in a suspension medium as in FIG. 4a, but absent any stabilizing agent of FIG. 4a after about three weeks as viewed by optical microscopy (oil immersion lens at 100×), in a form as would be detectable by a digital imaging hematology analyzer. As can be seen, there is substantial visible degradation. For example, at least the simulated monocytes show considerable transformation from their expected state when suspended in the suspension medium of the present teachings.

Figure 5:
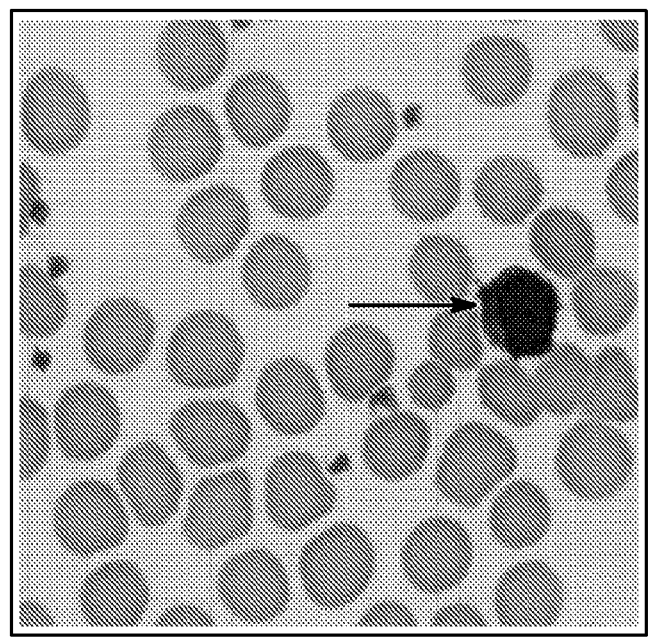
FIG. 5 is a micrograph to illustrate an example of a prior art hematology control, absent any stabilizing agent of the present teachings, as viewed by optical microscopy (oil immersion lens at 100×), in a form as would be analyzed by a digital imaging hematology analyzer.

FIG. 5 is a micrograph to illustrate an example of a prior art hematology control, absent any stabilizing agent of the present teachings, as viewed by optical microscopy (oil immersion lens at 100×), in a form as would be analyzed by a digital imaging hematology analyzer. It can be seen how nuclear matter is not identifiable.

EXAMPLES

Other benefits and advantages of the teachings will be understood upon review of the following Examples, which provide additional illustrative details of the present teachings.

Example 1

The suspension composition of Table 1 is prepared and predetermined amounts of simulated blood cells is added into it. Water makes up the balance. Concentrations are expressed in weight/volume percentages. To the suspension composition, simulated blood cell components are added according to three different predetermined amounts for each to form a resulting control composition. The three amounts correspond respectively to three different levels—a low abnormal level ("L.1"), a normal healthy level ("L.2") and a high abnormal level ("L.3"). A stability study is performed. The amounts for each leukocyte sub-population reported are provided in numbers (#) and percentage of the overall leukocyte population (%). Measurements are taken at the time the resulting control composition, day 56 of the study and day 105 of the study. The data are collected on a Roche Cobas m511 hematology Analyzer. After preparation of the resulting control composition, and throughout the duration of the study, the resulting control composition is maintained at a temperature of from about 2 to about 10° C. The results show that the suspension medium contributes to stability of the simulated blood cell components of the resulting control composition. This is consistent with the comparative images of FIGS. 3a and 3b.

TABLE 1

| Ingredient | Concentration (Pre-cell Addition)(w/v %) |
|---|---|
| EDTA, Disodium | 1.10% |
| Magnesium Chloride | 0.03% |
| HEPES | 1.19% |
| Calcium Acetate | 0.05% |
| Polyethylene Glycol 20,000 | 1.00% |
| Urea | 0.50% |
| Sodium Chloride | 2.64% |
| Chloramphenicol | 0.01% |
| Sodium Azide | 0.10% |
| Bovine Serum Albumin | 1.00% |
| Chitosan Oligosaccharide | 0.50% |
| Sodium Hydroxide | 0.18% |

The composition is analyzed using a Roche Cobas m511™ analyzer, with all levels analyzed in triplicate and reported as the average of the three analyses. Tests are performed on two lots of compositions. Results are reported in the below Tables 2 and 3, respectively for the first lot and the second lot.

TABLE 2

| | Day# | 0 | 56 | 105 | | Day# | 0 | 56 | 105 | | Day# | 0 | 56 | 105 |
|---|---|---|---|---|---|---|---|---|---|---|---|---|---|---|
| L.1 | WBC | 15.92 | 15.67 | 15.33 | L.2 | WBC | 8.00 | 7.45 | 7.77 | L.3 | WBC | 2.40 | 2.17 | 2.25 |
| | RBC | 2.25 | 2.33 | 2.35 | | RBC | 4.04 | 3.97 | 4.10 | | RBC | 5.06 | 5.15 | 5.36 |
| | HGB | 5.2 | 5.1 | 5.2 | | HGB | 10.8 | 10.5 | 10.9 | | HGB | 16.4 | 16.6 | 17.1 |
| | HCT | 15.5 | 15.5 | 15.8 | | HCT | 31.7 | 30.7 | 31.8 | | HCT | 46.0 | 46.4 | 48.3 |
| | MCV | 69.0 | 66.6 | 67.2 | | MCV | 78.3 | 77.2 | 77.6 | | MCV | 90.9 | 90.0 | 90.1 |
| | MCH | 22.9 | 22.1 | 22.1 | | MCH | 26.8 | 26.5 | 26.7 | | MCH | 32.4 | 32.1 | 31.9 |
| | MCHC | 33.1 | 33.2 | 32.8 | | MCHC | 34.2 | 34.3 | 34.4 | | MCHC | 35.7 | 35.7 | 35.4 |
| | PLT | 432 | 453 | 467 | | PLT | 198 | 221 | 204 | | PLT | 56 | 65 | 61 |
| | RDW | 15.6 | 15.9 | 16.2 | | RDW | 14.0 | 14.5 | 14.1 | | RDW | 12.9 | 12.5 | 12.5 |

TABLE 2-continued

|  | Day# | 0 | 56 | 105 |  | Day# | 0 | 56 | 105 |  | Day# | 0 | 56 | 105 |
|---|---|---|---|---|---|---|---|---|---|---|---|---|---|---|
| SD | RDW | 38.8 | 38.2 | 39.3 | SD | RDW | 39.4 | 40.3 | 39.5 | SD | RDW | 42.2 | 40.7 | 40.5 |
|  | MPV | 9.8 | 9.9 | 9.7 |  | MPV | 9.5 | 9.2 | 9.3 |  | MPV | 8.9 | 9.2 | 9.3 |
| % | nRBC | 0.3 | 0.1 | 0.1 | % | nRBC | 19.5 | 18.6 | 13.6 | % | nRBC | 10.9 | 10.6 | 9.9 |
| # | nRBC | 0.0 | 0.0 | 0.0 | # | nRBC | 1.6 | 1.4 | 1.1 | # | nRBC | 0.3 | 0.2 | 0.2 |
| % | RETIC | 7.04 | 7.29 | 6.78 | % | RETIC | 3.93 | 3.53 | 2.60 | % | RETIC | 0.84 | 0.65 | 0.21 |
| # | RETIC | 0.16 | 0.18 | 0.16 | # | RETIC | 0.16 | 0.14 | 0.11 | # | RETIC | 0.04 | 0.04 | 0.01 |
| % | NEUT | 59.9 | 59.6 | 55.4 | % | NEUT | 59.2 | 58.3 | 56.4 | % | NEUT | 59.1 | 59.0 | 58.6 |
| # | NEUT | 9.54 | 9.36 | 8.50 | # | NEUT | 4.74 | 4.35 | 4.38 | # | NEUT | 1.42 | 1.28 | 1.32 |
| % | LYM | 22.6 | 22.1 | 24.1 | % | LYM | 22.5 | 23.3 | 23.9 | % | LYM | 22.4 | 20.5 | 21.6 |
| # | LYM | 3.60 | 3.46 | 3.70 | # | LYM | 1.80 | 1.74 | 1.86 | # | LYM | 0.54 | 0.45 | 0.49 |
| % | MONO | 10.1 | 9.1 | 10.1 | % | MONO | 12.8 | 12.8 | 13.0 | % | MONO | 14.7 | 16.1 | 16.2 |
| # | MONO | 1.60 | 1.43 | 1.55 | # | MONO | 1.03 | 0.96 | 1.01 | # | MONO | 0.35 | 0.35 | 0.36 |
| % | EOS | 7.1 | 8.5 | 9.7 | % | EOS | 5.0 | 4.7 | 6.1 | % | EOS | 3.5 | 3.9 | 3.2 |
| # | EOS | 1.12 | 1.33 | 1.48 | # | EOS | 0.40 | 0.35 | 0.47 | # | EOS | 0.08 | 0.08 | 0.07 |
| % | BASO | 0.4 | 0.7 | 0.7 | % | BASO | 0.4 | 0.8 | 0.7 | % | BASO | 0.2 | 0.5 | 0.5 |
| # | BASO | 0.06 | 0.10 | 0.10 | # | BASO | 0.03 | 0.06 | 0.05 | # | BASO | 0.01 | 0.01 | 0.01 |

TABLE 3

|  | Day# | 0 | 52 | 105 |  | Day# | 0 | 52 | 105 |  | Day# | 0 | 52 | 105 |
|---|---|---|---|---|---|---|---|---|---|---|---|---|---|---|
| L.1 | WBC | 18.60 | 19.29 | 18.90 | L.2 | WBC | 9.20 | 9.18 | 9.12 | L.3 | WBC | 2.71 | 2.85 | 2.67 |
|  | RBC | 2.48 | 2.52 | 2.44 |  | RBC | 4.29 | 4.35 | 4.18 |  | RBC | 5.36 | 5.54 | 5.42 |
|  | HGB | 5.9 | 6.1 | 5.9 |  | HGB | 11.7 | 11.8 | 11.4 |  | HGB | 17.9 | 18.4 | 18.0 |
|  | HCT | 17.5 | 18.0 | 17.4 |  | HCT | 33.5 | 33.9 | 33.1 |  | HCT | 49.4 | 50.8 | 50.1 |
|  | MCV | 70.7 | 71.3 | 71.1 |  | MCV | 78.1 | 78.0 | 79.1 |  | MCV | 92.2 | 91.6 | 92.4 |
|  | MCH | 23.9 | 24.2 | 24.2 |  | MCH | 27.2 | 27.1 | 27.3 |  | MCH | 33.4 | 33.2 | 33.4 |
|  | MCHC | 33.8 | 34.0 | 34.0 |  | MCHC | 34.9 | 34.8 | 34.6 |  | MCHC | 36.2 | 36.2 | 36.1 |
|  | PLT | 576 | 583 | 559 |  | PLT | 261 | 272 | 252 |  | PLT | 76 | 81 | 80 |
|  | RDW | 14.4 | 13.8 | 13.8 |  | RDW | 12.4 | 11.6 | 11.6 |  | RDW | 10.6 | 9.4 | 9.9 |
| StDev | RDW | 36.7 | 35.2 | 35.3 | StDev | RDW | 34.8 | 32.6 | 33.0 | StDev | RDW | 35.1 | 30.9 | 33.0 |
|  | MPV | 8.6 | 8.5 | 8.1 |  | MPV | 8.7 | 8.4 | 8.1 |  | MPV | 8.7 | 8.7 | 8.3 |
| % | nRBC | 0.0 | 0.1 | 0.0 | % | nRBC | 20.2 | 19.5 | 18.8 | % | nRBC | 10.8 | 10.5 | 11.1 |
| # | nRBC | 0.0 | 0.0 | 0.0 | # | nRBC | 1.9 | 1.8 | 1.7 | # | nRBC | 0.3 | 0.3 | 0.3 |
| % | RETIC | 5.15 | 4.36 | 4.06 | % | RETIC | 1.89 | 2.10 | 1.84 | % | RETIC | 0.02 | 0.03 | 0.00 |
| # | RETIC | 0.13 | 0.11 | 0.10 | # | RETIC | 0.08 | 0.09 | 0.08 | # | RETIC | 0.00 | 0.00 | 0.00 |
| % | NEUT | 59.8 | 59.0 | 61.3 | % | NEUT | 60.7 | 59.5 | 61.9 | % | NEUT | 59.6 | 59.1 | 59.4 |
| # | NEUT | 11.12 | 11.38 | 11.58 | # | NEUT | 5.58 | 5.46 | 5.65 | # | NEUT | 1.62 | 1.69 | 1.58 |
| % | LYM | 37.3 | 38.9 | 35.8 | % | LYM | 36.2 | 37.1 | 35.0 | % | LYM | 35.2 | 35.9 | 36.6 |
| # | LYM | 6.94 | 7.51 | 6.76 | # | LYM | 3.33 | 3.41 | 3.20 | # | LYM | 0.95 | 1.03 | 0.95 |
| % | MONO | 2.2 | 1.6 | 2.4 | % | MONO | 2.3 | 3.0 | 2.5 | % | MONO | 3.4 | 3.9 | 3.6 |
| # | MONO | 0.41 | 0.30 | 0.46 | # | MONO | 0.22 | 0.28 | 0.23 | # | MONO | 0.09 | 0.11 | 0.09 |
| % | EOS | 0.6 | 0.5 | 0.4 | % | EOS | 0.5 | 0.2 | 0.4 | % | EOS | 1.4 | 1.1 | 1.4 |
| # | EOS | 0.11 | 0.09 | 0.08 | # | EOS | 0.05 | 0.02 | 0.03 | # | EOS | 0.04 | 0.03 | 0.04 |
| % | BASO | 0.1 | 0.2 | 0.1 | % | BASO | 0.2 | 0.2 | 0.2 | % | BASO | 0.1 | 0.1 | 0.0 |
| # | BASO | 0.02 | 0.03 | 0.02 | # | BASO | 0.01 | 0.02 | 0.01 | # | BASO | 0.00 | 0.00 | 0.00 |

For the above tables the following abbreviations are used: WBC: white blood cell; RBC: red blood cell; HGB: hemoglobin; HCT: hematocrit; MCV: mean corpuscular volume; MCH: mean corpuscular mass; MCHC: mean corpuscular hemoglobin concentration; PLT: platelet; RDW: red blood cell distribution width; SD RDW: standard deviation for red blood cell distribution width; MPV: mean platelet volume; nRBC: nucleated red blood cell; RETIC: reticulocyte; NEUT: neutrophil; LYM: lymphocyte; MONO: monocyte; EOS: eosinophil; BASO: basophil.

General Remarks Applicable to All Teachings

As used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51 , 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the comparative teaching of amounts expressed as weight/volume percent for two or more ingredients also encompasses relative weight proportions of the two or more ingredients to each other, even if not expressly stated. For example, if a teaching recites 2% A, and 5% B, then the teaching also encompasses a weight ratio of A:B of 2:5. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of (namely, the presence of any additional elements, ingredients, components or steps, does not materially affect the properties and/or benefits derived from the teachings; or even consist of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A suspension composition comprising:
   one or more simulated blood components;
   a buffered aqueous solution; and
   at least one stabilizing agent, wherein the at least one stabilizing agent includes one or any combination of chitin, a salt of chitin, a derivative of chitin, a chitosan, a salt of a chitosan, or a derivative of a chitosan, and wherein the one or more simulated blood components are derived from processed blood cells.

2. The suspension composition of claim 1, wherein the suspension composition is adapted for use in digital imaging hematology instrument that creates and analyzes an image by a computer implemented technique of a sample that has been dispensed onto a substrate.

3. The suspension composition of claim 1, wherein the suspension composition is adapted, upon mixing with the one or more simulated blood components, for dispensing through a nozzle for delivery by printing to a transparent substrate and subsequent analysis by a digital imaging hematology analyzer.

4. The suspension composition of claim 1, wherein the at least one stabilizing agent is present in an amount sufficient for preserving stability of the detectable morphological characteristics of the one or more simulated blood components for a period of at least 30 days, after being stored during such period at about 2 to about 10° C., upon suspending the blood components; wherein the one or more simulated blood components include nucleated blood cells, and wherein the detectable morphological characteristics that are preserved include size, a nucleus morphology and morphology of other native nuclear cytoplasm granules.

5. The suspension composition of claim 1, wherein the aqueous buffered solution includes at least one buffering agent, and at least one antimicrobial.

6. The suspension composition of claim 1, wherein the aqueous buffered solution includes at least one dispersion agent for reducing aggregation of the one or more simulated blood components as compared with the aqueous buffered solution without the dispersion agent.

7. The suspension composition of claim 1, wherein the suspension composition has a pH ranging from about 6 to about 8.

8. The suspension composition of claim 1, wherein the at least one stabilizing agent is selected from chitosan acetate, chitosan lactate, chitosan oligosaccharide, carboxyl methyl chitosan, or any combination thereof.

9. The suspension composition of claim 1, wherein the at least one stabilizing agent is present in an amount up to about ten percent (10%) of the suspension composition.

10. The suspension composition of claim 1, wherein the one or more simulated blood components include simulated nucleated leukocytes, nucleated red blood cells or both.

11. The suspension composition of claim 1, wherein the at least one stabilizing agent is present in an amount up to about ten percent (10%) of a resulting control composition admixture including the suspension composition and the simulated blood cells.

12. The suspension composition of claim 1, wherein the suspension composition and any resulting control composition employing the suspension composition is substantially free of any added lipoprotein.

13. A method of using the suspension composition of claim 2, comprising a step of dispensing the suspension composition onto a substrate, and at least partially evaporating water from the aqueous buffered suspension composition.

14. The suspension composition of claim 1, wherein the at least one stabilizing agent is present in an amount up to about seven percent (7%) of the suspension composition.

15. The suspension composition of claim 1, wherein the at least one stabilizing agent is present in an amount of about five percent (5%) of the suspension composition.

16. The suspension composition of claim 1, wherein the one or more simulated blood components comprises one or any combination of components for simulating a platelet, a reticulated platelet, a red blood cell, reticulocyte, an immature reticulocyte, a nucleated red blood cell, or a simulated leukocyte population or sub-population.

17. The suspension composition of claim 1, wherein the amount of the one or more simulated blood components is a known amount for simulating a normal amount in whole blood.

18. The method of claim 13, further comprising creating and analyzing an image of the suspension composition in a digital imaging hematology instrument.

19. The suspension composition of claim 1, wherein the at least one stabilizing agent is present in an amount sufficient for preserving stability of detectable morphological characteristics of the one or more simulated blood components for a period of at least 3 days, after being stored during such period at about 2 to about 10° C., upon suspending the one or more simulated blood components.

20. The suspension composition of claim 1, wherein the one or more simulated blood components comprises neutrophils, lymphocytes, and monocytes.

21. The suspension composition of claim 1, wherein the one or more simulated blood components comprises neutrophils, eosinophils, basophils, lymphocytes, and monocytes.

* * * * *